United States Patent
Johnson et al.

(10) Patent No.: US 10,722,798 B1
(45) Date of Patent: *Jul. 28, 2020

(54) TASK-BASED CONTENT MANAGEMENT

(71) Applicant: Amazon Technologies, Inc., Seattle, WA (US)

(72) Inventors: Brett Ethan Johnson, Woodinville, WA (US); Robert Duane Rost, Seattle, WA (US); Matthew James Van Gorder, Redmond, WA (US); Thomas Richard Leonard, Seattle, WA (US)

(73) Assignee: Amazon Technologies, Inc., Seattle, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/645,082

(22) Filed: Jul. 10, 2017

Related U.S. Application Data

(63) Continuation of application No. 14/299,712, filed on Jun. 9, 2014, now Pat. No. 9,731,192.

(51) Int. Cl.
| | |
|---|---|
| *A63F 9/24* | (2006.01) |
| *A63F 11/00* | (2006.01) |
| *G06F 13/00* | (2006.01) |
| *G06F 17/00* | (2019.01) |
| *A63F 13/55* | (2014.01) |

(52) U.S. Cl.
CPC .................................. *A63F 13/55* (2014.09)

(58) Field of Classification Search
USPC ............... 463/20, 22, 23, 27, 31, 39, 40, 42; 273/236
See application file for complete search history.

(56) References Cited

U.S. PATENT DOCUMENTS

| | | |
|---|---|---|
| 4,679,789 A | 7/1987 | Okada |
| 6,106,395 A | 8/2000 | Begis |
| 2011/0272883 A1 | 11/2011 | Fox |
| 2011/0275431 A1* | 11/2011 | Hirzel .................... A63F 13/46 463/23 |
| 2012/0115579 A1 | 5/2012 | Buecheler et al. |
| 2013/0225260 A1 | 8/2013 | Cudak et al. |
| 2014/0031129 A1 | 1/2014 | Morrison et al. |

* cited by examiner

*Primary Examiner* — Adetokunbo O Torimiro
(74) *Attorney, Agent, or Firm* — BakerHostetler

(57) ABSTRACT

In some cases, one or more tasks may be selected for inclusion within a content item or portions of a content item such as different story arcs. Each such task may be completed based, at least in part, on an associated set of one or more actions and an associated set of one or more parameters. Also, in some cases, one or more node layouts may be generated in association with a content item or portions of a content item. Each node within a node layout may, for example, have at least one associated task within a respective content item or content item portion.

20 Claims, 18 Drawing Sheets

US 10,722,798 B1

TASK-BASED CONTENT MANAGEMENT

CROSS REFERENCE TO RELATED APPLICATION

This application is a continuation of U.S. patent application Ser. No. 14/299,712 filed on Jun. 9, 2014, the disclosure of which is hereby incorporated by reference in its entirety. This application is also related to U.S. patent application Ser. No. 14/299,793 filed Jun. 9, 2014, entitled "TASK-BASED CONTENT MANAGEMENT", now issued as U.S. Pat. No. 9,358,464, the disclosure of which is also hereby incorporated by reference in its entirety.

BACKGROUND

Multi-participant content items, such as multiplayer video games, are becoming increasingly popular and widespread. As an example, multiplayer video games, such as massively multiplayer online (MMO) games, may, in some cases, enable large numbers of players from multiple remote locations to engage in related gaming experiences. Different players may sometimes participate in such games as individual characters or as members of a group, such as a team or faction. Individual players and groups may often compete against rival players and groups for control of geographic regions, weapons, financial resources and other goods and resources. Multi-participant content items may sometimes be played over long time durations, within which different participants may join, exit and, in some cases, rejoin the content item multiple times.

There are a number of characteristics associated with multi-participant content items that may change dynamically before, during and after the content items are played. These changes may sometimes occur rapidly and on a large scale basis. For example, the quantity of participants and other participant characteristics may be subject to change. As an example, a content item may start out with only 5 participants, but that number may quickly rise to 500 and, in turn, to 5,000 or even 50,000 participants or more. In addition to participant quantity, the skill level, play style, performance, preferences, interests, demographics and other participant characteristics may also be subject to change. In addition to the examples set forth above, many other characteristics associated with multi-participant content items may also be subject to change.

BRIEF DESCRIPTION OF DRAWINGS

The following detailed description may be better understood when read in conjunction with the appended drawings. For the purposes of illustration, there are shown in the drawings example embodiments of various aspects of the disclosure; however, the invention is not limited to the specific methods and instrumentalities disclosed.

DETAILED DESCRIPTION

Figure 1:
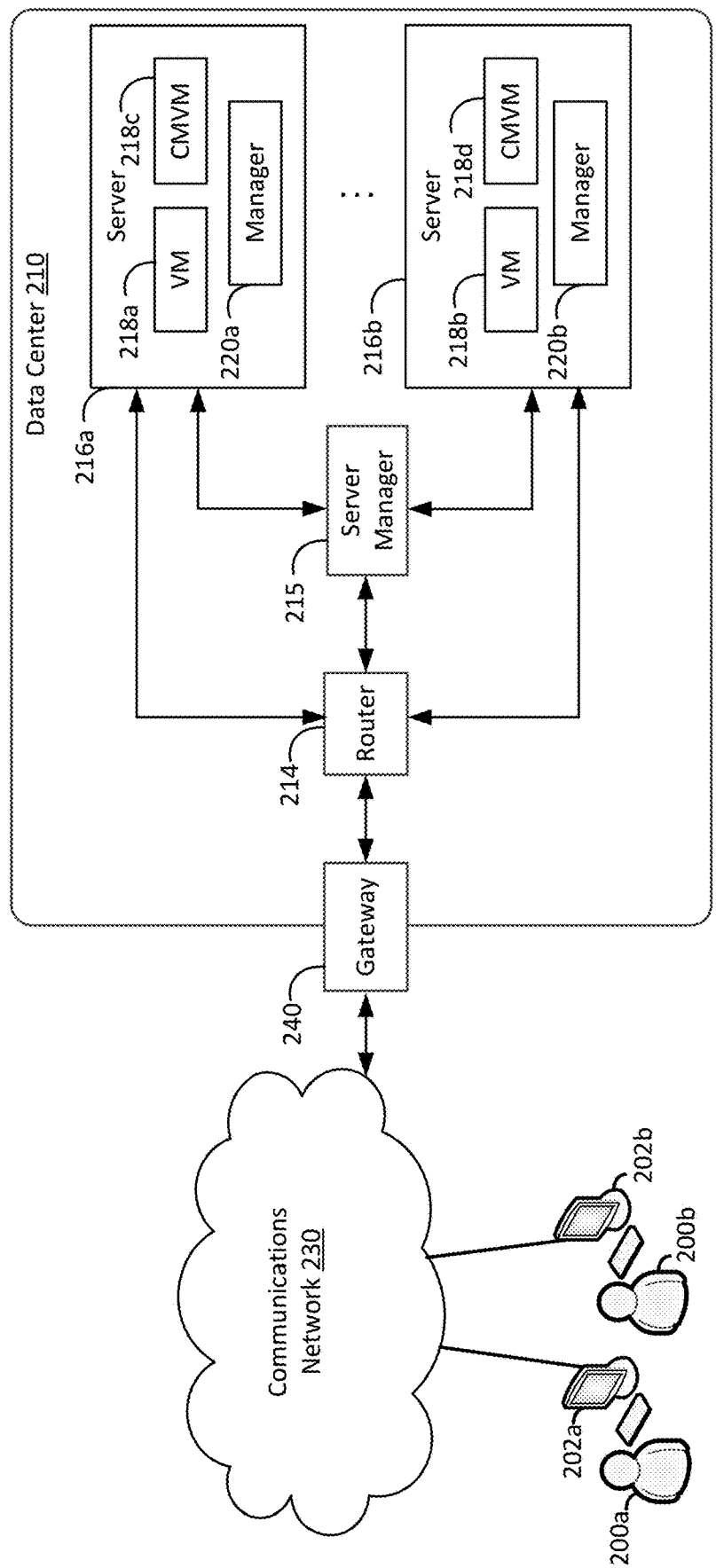
FIG. 1 is a diagram illustrating an example computing system that may be used in some embodiments.

Various techniques for content management are disclosed herein. The disclosed techniques may be used, for example, for management of multi-participant content items such as multiplayer video games. In some cases, one or more tasks may be selected for inclusion within a content item or portions of a content item such as different story arcs. Each such task may be completed based, at least in part, on an associated set of one or more actions and an associated set of one or more parameters. The actions associated with a task may, for example, correspond to actions that may be performed by one or more participants as part of the task. For example, a task to attack a bridge may include actions such as: obtain explosive, avoid bridge security, plant explosive and detonate explosive. The parameters associated with a task may, for example, correspond to rules or other conditions associated with the task. Some example parameters may include a number of participants required to complete various actions, an allowed time limit within which to complete various actions, various alternative action paths, sequential relationships between actions, various levels of progress for completing a task and the like.

Additionally, in some cases, one or more node layouts may be generated in association with a content item or portions of a content item. Each node within a node layout may, for example, have at least one associated task within a respective content item or content item portion. The node layout may, for example, at least partially indicate one or more relationships between two or more nodes within the node layout. A relationship between nodes may be based on, for example, virtual geography corresponding to tasks associated with the nodes. A relationship between nodes may also be based on, for example, an availability of a task associated with one node being based, at least in part, on a completion of one or more other tasks associated with one or more other nodes. In some cases, an indication may be maintained of whether a task associated with each node is available to at least one participant or is not available to any participants. Also, in some cases, an indication may be maintained of whether a task associated with each node has been completed or has not yet been completed.

In some cases, information corresponding to various content item characteristics may be collected before, during and/or after a playing of a content item. The content item characteristics may include, for example, participant characteristics, task characteristics, various timing measurements and other characteristics associated with a content item. Participant characteristics may include, for example, participant quantity, participant skill level, participant preferences, participant interests, participant demographics, participant performance, participant progress, participant play style and the like. The task characteristics may include, for example, associated actions and parameters, a number of participants currently performing each task, a progress of completion, an elapsed time since initiation, a time limit, a preferred skill level, an associated play style, suggested demographics, a description, associated virtual geography, other associated requirements and the like. The content item characteristics may be aggregated over various levels or combinations of levels, such as individual participants, teams, factions and other participant groups, all participants, individual actions, groups of actions, individual tasks, groups of tasks, story arcs, node layouts and others. In some cases, the collected content item characteristic information may be used to add, change and/or remove one or more tasks within a content item or content item portion. Also, in some cases, the collected content item characteristic information may be used to add, change and/or remove actions and/or parameters associated with a task. Furthermore, in some cases, the collected content item characteristic information may be used to generate and adjust various node layouts, such as by adding, changing or deleting nodes and by defining or changing a relationship between one or more nodes.

A content provider may, in some cases, render and transmit content items to participants at client devices over an electronic network, such as the Internet. Content items may, in some cases, be provided upon request to clients using, for example, streaming content delivery techniques. An example computing environment that enables providing of content to clients will now be described in detail. In particular, FIG. 1 illustrates an example computing environment in which the embodiments described herein may be implemented. FIG. 1 is a diagram schematically illustrating an example of a data center 210 that can provide computing resources to users 200a and 200b (which may be referred herein singularly as user 200 or in the plural as users 200) via user computers 202a and 202b (which may be referred herein singularly as computer 202 or in the plural as computers 202) via a communications network 230. Data center 210 may be configured to provide computing resources for executing applications on a permanent or an as-needed basis. The computing resources provided by data center 210 may include various types of resources, such as gateway resources, load balancing resources, routing resources, networking resources, computing resources, volatile and non-volatile memory resources, content delivery resources, data processing resources, data storage resources, data communication resources and the like. Each type of computing resource may be general-purpose or may be available in a number of specific configurations. For example, data processing resources may be available as virtual machine instances that may be configured to provide various web services. In addition, combinations of resources may be made available via a network and may be configured as one or more web services. The instances may be configured to execute applications, including web services, such as application services, media services, database services, processing services, gateway services, storage services, routing services, security services, encryption services, load balancing services, application services and the like. These services may be configurable with set or custom applications and may be configurable in size, execution, cost, latency, type, duration, accessibility and in any other dimension. These web services may be configured as available infrastructure for one or more clients and can include one or more applications configured as a platform or as software for one or more clients. These web services may be made available via one or more communications protocols. These communications protocols may include, for example, hypertext transfer protocol (HTTP) or non-HTTP protocols. These communications protocols may also include, for example, more reliable transport layer protocols, such as transmission control protocol (TCP), and less reliable transport layer protocols, such as user datagram protocol (UDP). Data storage resources may include file storage devices, block storage devices and the like.

Each type or configuration of computing resource may be available in different sizes, such as large resources—consisting of many processors, large amounts of memory and/or large storage capacity—and small resources—consisting of fewer processors, smaller amounts of memory and/or smaller storage capacity. Customers may choose to allocate a number of small processing resources as web servers and/or one large processing resource as a database server, for example.

Data center 210 may include servers 216a and 216b (which may be referred herein singularly as server 216 or in the plural as servers 216) that provide computing resources. These resources may be available as bare metal resources or as virtual machine instances 218a-d (which may be referred herein singularly as virtual machine instance 218 or in the plural as virtual machine instances 218). Virtual machine instances 218c and 218d are content management virtual machine ("CMVM") instances. The CMVM virtual machine instances 218c and 218d may be configured to perform all, or any portion, of the content management techniques and/or any other of the disclosed techniques in accordance with the present disclosure and described in detail below. As should be appreciated, while the particular example illustrated in FIG. 1 includes one CMVM virtual machine in each server, this is merely an example. A server may include more than one CMVM virtual machine or may not include any CMVM virtual machines.

The availability of virtualization technologies for computing hardware has afforded benefits for providing large scale computing resources for customers and allowing computing resources to be efficiently and securely shared between multiple customers. For example, virtualization technologies may allow a physical computing device to be shared among multiple users by providing each user with one or more virtual machine instances hosted by the physical computing device. A virtual machine instance may be a software emulation of a particular physical computing system that acts as a distinct logical computing system. Such a virtual machine instance provides isolation among multiple operating systems sharing a given physical computing resource. Furthermore, some virtualization technologies may provide virtual resources that span one or more physical resources, such as a single virtual machine instance with multiple virtual processors that span multiple distinct physical computing systems.

Referring to FIG. 1, communications network 230 may, for example, be a publicly accessible network of linked networks and possibly operated by various distinct parties, such as the Internet. In other embodiments, communications network 230 may be a private network, such as a corporate or university network that is wholly or partially inaccessible to non-privileged users. In still other embodiments, communications network 230 may include one or more private networks with access to and/or from the Internet.

Communication network 230 may provide access to computers 202. User computers 202 may be computers utilized by users 200 or other customers of data center 210. For instance, user computer 202a or 202b may be a server, a desktop or laptop personal computer, a tablet computer, a wireless telephone, a personal digital assistant (PDA), an e-book reader, a game console, a set-top box or any other computing device capable of accessing data center 210. User computer 202a or 202b may connect directly to the Internet (e.g., via a cable modem or a Digital Subscriber Line (DSL)). Although only two user computers 202a and 202b are depicted, it should be appreciated that there may be multiple user computers.

User computers 202 may also be utilized to configure aspects of the computing resources provided by data center 210. In this regard, data center 210 might provide a gateway or web interface through which aspects of its operation may be configured through the use of a web browser application program executing on user computer 202. Alternately, a stand-alone application program executing on user computer 202 might access an application programming interface (API) exposed by data center 210 for performing the configuration operations. Other mechanisms for configuring the operation of various web services available at data center 210 might also be utilized.

Servers 216 shown in FIG. 1 may be standard servers configured appropriately for providing the computing resources described above and may provide computing resources for executing one or more web services and/or applications. In one embodiment, the computing resources may be virtual machine instances 218. In the example of virtual machine instances, each of the servers 216 may be configured to execute an instance manager 220a or 220b (which may be referred herein singularly as instance manager 220 or in the plural as instance managers 220) capable of executing the virtual machine instances 218. The instance managers 220 may be a virtual machine monitor (VMM) or another type of program configured to enable the execution of virtual machine instances 218 on server 216, for example. As discussed above, each of the virtual machine instances 218 may be configured to execute all or a portion of an application.

It should be appreciated that although the embodiments disclosed above discuss the context of virtual machine instances, other types of implementations can be utilized with the concepts and technologies disclosed herein. For example, the embodiments disclosed herein might also be utilized with computing systems that do not utilize virtual machine instances.

In the example data center 210 shown in FIG. 1, a router 214 may be utilized to interconnect the servers 216a and 216b. Router 214 may also be connected to gateway 240, which is connected to communications network 230. Router 214 may be connected to one or more load balancers, and alone or in combination may manage communications within networks in data center 210, for example, by forwarding packets or other data communications as appropriate based on characteristics of such communications (e.g., header information including source and/or destination addresses, protocol identifiers, size, processing requirements, etc.) and/or the characteristics of the private network (e.g., routes based on network topology, etc.). It will be appreciated that, for the sake of simplicity, various aspects of the computing systems and other devices of this example are illustrated without showing certain conventional details. Additional computing systems and other devices may be interconnected in other embodiments and may be interconnected in different ways.

In the example data center 210 shown in FIG. 1, a server manager 215 is also employed to at least in part direct various communications to, from and/or between servers 216a and 216b. While FIG. 1 depicts router 214 positioned between gateway 240 and server manager 215, this is merely an exemplary configuration. In some cases, for example, server manager 215 may be positioned between gateway 240 and router 214. Server manager 215 may, in some cases, examine portions of incoming communications from user computers 202 to determine one or more appropriate servers 216 to receive and/or process the incoming communications. Server manager 215 may determine appropriate servers to receive and/or process the incoming communications based on factors such as an identity, location or other attributes associated with user computers 202, a nature of a task with which the communications are associated, a priority of a task with which the communications are associated, a duration of a task with which the communications are associated, a size and/or estimated resource usage of a task with which the communications are associated and many other factors. Server manager 215 may, for example, collect or otherwise have access to state information and other information associated with various tasks in order to, for example, assist in managing communications and other operations associated with such tasks.

It should be appreciated that the network topology illustrated in FIG. 1 has been greatly simplified and that many more networks and networking devices may be utilized to interconnect the various computing systems disclosed herein. These network topologies and devices should be apparent to those skilled in the art.

It should also be appreciated that data center 210 described in FIG. 1 is merely illustrative and that other implementations might be utilized. Additionally, it should be appreciated that the functionality disclosed herein might be implemented in software, hardware or a combination of software and hardware. Other implementations should be apparent to those skilled in the art. It should also be appreciated that a server, gateway or other computing device may comprise any combination of hardware or software that can interact and perform the described types of functionality, including without limitation desktop or other computers, database servers, network storage devices and other network devices, PDAs, tablets, cellphones, wireless phones, pagers, electronic organizers, Internet appliances, television-based systems (e.g., using set top boxes and/or personal/digital video recorders) and various other consumer products that include appropriate communication capabilities. In addition, the functionality provided by the illustrated modules may in some embodiments be combined in fewer modules or distributed in additional modules. Similarly, in some embodiments the functionality of some of the illustrated modules may not be provided and/or other additional functionality may be available.

Figure 2:
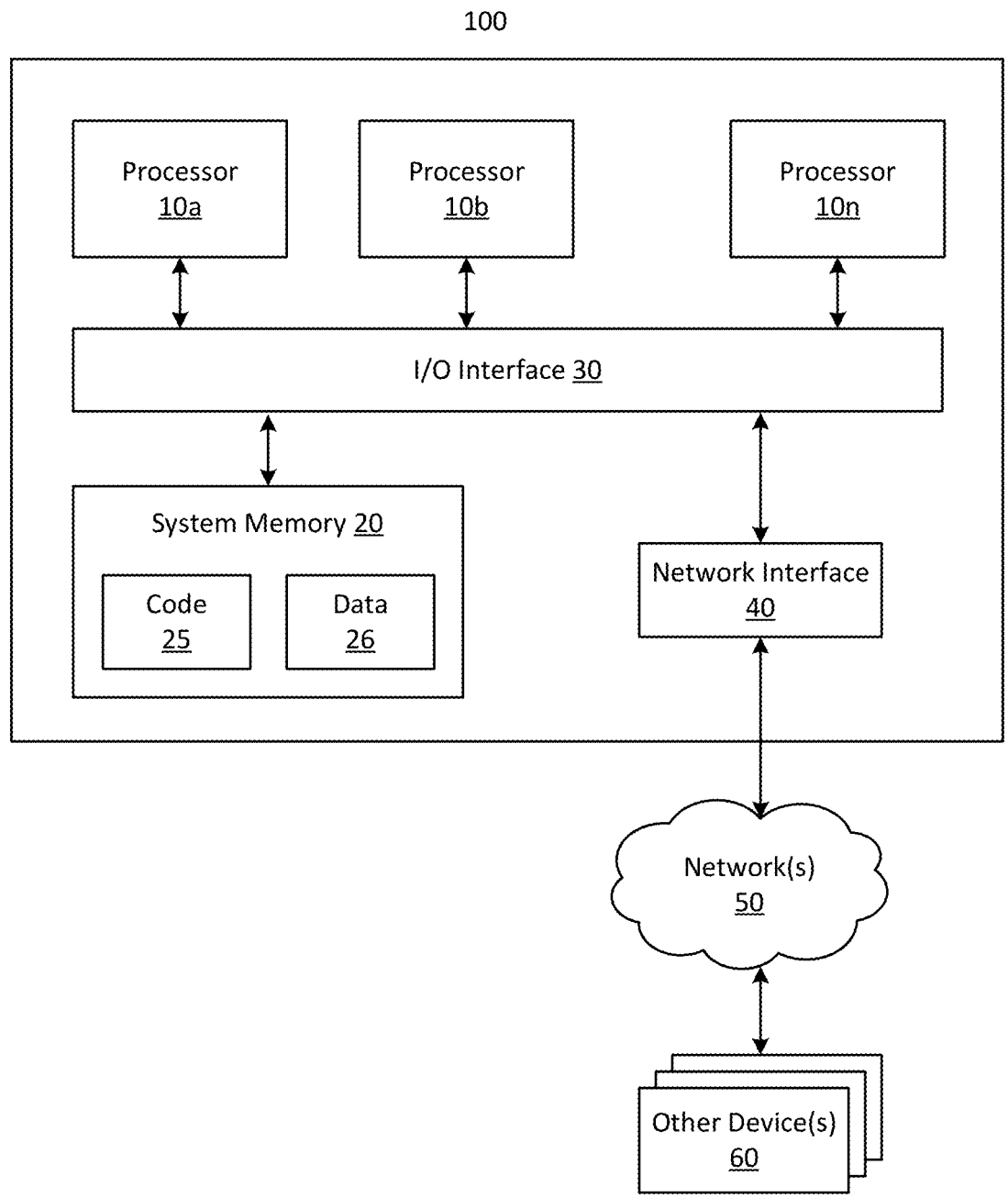
FIG. 2 is a diagram illustrating an example computing system that may be used in some embodiments.

In at least some embodiments, a server that implements a portion or all of one or more of the technologies described herein may include a general-purpose computer system that includes or is configured to access one or more computer-accessible media. FIG. 2 depicts a general-purpose computer system that includes or is configured to access one or more computer-accessible media. In the illustrated embodiment, computing device 100 includes one or more processors 10a, 10b and/or 10n (which may be referred herein singularly as "a processor 10" or in the plural as "the processors 10") coupled to a system memory 20 via an input/output (I/O) interface 30. Computing device 100 further includes a network interface 40 coupled to I/O interface 30.

In various embodiments, computing device 100 may be a uniprocessor system including one processor 10 or a multiprocessor system including several processors 10 (e.g., two, four, eight or another suitable number). Processors 10 may be any suitable processors capable of executing instructions. For example, in various embodiments, processors 10 may be general-purpose or embedded processors implementing any of a variety of instruction set architectures (ISAs), such as the x86, PowerPC, SPARC or MIPS ISAs or any other suitable ISA. In multiprocessor systems, each of processors 10 may commonly, but not necessarily, implement the same ISA.

System memory 20 may be configured to store instructions and data accessible by processor(s) 10. In various embodiments, system memory 20 may be implemented using any suitable memory technology, such as static random access memory (SRAM), synchronous dynamic RAM (SDRAM), nonvolatile/Flash®-type memory or any other type of memory. In the illustrated embodiment, program instructions and data implementing one or more desired functions, such as those methods, techniques and data described above, are shown stored within system memory 20 as code 25 and data 26.

In one embodiment, I/O interface 30 may be configured to coordinate I/O traffic between processor 10, system memory 20 and any peripherals in the device, including network interface 40 or other peripheral interfaces. In some embodiments, I/O interface 30 may perform any necessary protocol, timing or other data transformations to convert data signals from one component (e.g., system memory 20) into a format suitable for use by another component (e.g., processor 10). In some embodiments, I/O interface 30 may include support for devices attached through various types of peripheral buses, such as a variant of the Peripheral Component Interconnect (PCI) bus standard or the Universal Serial Bus (USB) standard, for example. In some embodiments, the function of I/O interface 30 may be split into two or more separate components, such as a north bridge and a south bridge, for example. Also, in some embodiments some or all of the functionality of I/O interface 30, such as an interface to system memory 20, may be incorporated directly into processor 10.

Network interface 40 may be configured to allow data to be exchanged between computing device 100 and other device or devices 60 attached to a network or networks 50, such as other computer systems or devices, for example. In various embodiments, network interface 40 may support communication via any suitable wired or wireless general data networks, such as types of Ethernet networks, for example. Additionally, network interface 40 may support communication via telecommunications/telephony networks, such as analog voice networks or digital fiber communications networks, via storage area networks such as Fibre Channel SANs (storage area networks) or via any other suitable type of network and/or protocol.

In some embodiments, system memory 20 may be one embodiment of a computer-accessible medium configured to store program instructions and data as described above for implementing embodiments of the corresponding methods and apparatus. However, in other embodiments, program instructions and/or data may be received, sent or stored upon different types of computer-accessible media. Generally speaking, a computer-accessible medium may include non-transitory storage media or memory media, such as magnetic or optical media—e.g., disk or DVD/CD coupled to computing device 100 via I/O interface 30. A non-transitory computer-accessible storage medium may also include any volatile or non-volatile media, such as RAM (e.g. SDRAM, DDR SDRAM, RDRAM, SRAM, etc.), ROM (read only memory) etc., that may be included in some embodiments of computing device 100 as system memory 20 or another type of memory. Further, a computer-accessible medium may include transmission media or signals such as electrical, electromagnetic or digital signals conveyed via a communication medium, such as a network and/or a wireless link, such as those that may be implemented via network interface 40. Portions or all of multiple computing devices, such as those illustrated in FIG. 2, may be used to implement the described functionality in various embodiments; for example, software components running on a variety of different devices and servers may collaborate to provide the functionality. In some embodiments, portions of the described functionality may be implemented using storage devices, network devices or special-purpose computer systems, in addition to or instead of being implemented using general-purpose computer systems. The term "computing device," as used herein, refers to at least all these types of devices and is not limited to these types of devices.

A compute node, which may be referred to also as a computing node, may be implemented on a wide variety of computing environments, such as commodity-hardware computers, virtual machines, web services, computing clusters and computing appliances. Any of these computing devices or environments may, for convenience, be described as compute nodes.

A network set up by an entity, such as a company or a public sector organization, to provide one or more web services (such as various types of cloud-based computing or storage) accessible via the Internet and/or other networks to a distributed set of clients may be termed a provider network. Such a provider network may include numerous data centers hosting various resource pools, such as collections of physical and/or virtualized computer servers, storage devices, networking equipment and the like, needed to implement and distribute the infrastructure and web services offered by the provider network. The resources may in some embodiments be offered to clients in various units related to the web service, such as an amount of storage capacity for storage, processing capability for processing, as instances, as sets of related services and the like. A virtual computing instance may, for example, comprise one or more servers with a specified computational capacity (which may be specified by indicating the type and number of CPUs, the main memory size and so on) and a specified software stack (e.g., a particular version of an operating system, which may in turn run on top of a hypervisor).

A number of different types of computing devices may be used singly or in combination to implement the resources of the provider network in different embodiments, including general-purpose or special-purpose computer servers, storage devices, network devices and the like. In some embodiments a client or user may be provided direct access to a resource instance, e.g., by giving a user an administrator login and password. In other embodiments the provider network operator may allow clients to specify execution requirements for specified client applications and schedule execution of the applications on behalf of the client on execution platforms (such as application server instances, Java™ virtual machines (JVMs), general-purpose or special-purpose operating systems, platforms that support various interpreted or compiled programming languages such as Ruby, Perl, Python, C, C++ and the like or high-performance computing platforms) suitable for the applications, without, for example, requiring the client to access an instance or an execution platform directly. A given execution platform may utilize one or more resource instances in some implementations; in other implementations, multiple execution platforms may be mapped to a single resource instance.

In many environments, operators of provider networks that implement different types of virtualized computing, storage and/or other network-accessible functionality may allow customers to reserve or purchase access to resources in various resource acquisition modes. The computing resource provider may provide facilities for customers to select and launch the desired computing resources, deploy application components to the computing resources and maintain an application executing in the environment. In addition, the computing resource provider may provide further facilities for the customer to quickly and easily scale up or scale down the numbers and types of resources allocated to the application, either manually or through automatic scaling, as demand for or capacity requirements of the application change. The computing resources provided by the computing resource provider may be made available in discrete units, which may be referred to as instances. An instance may represent a physical server hardware platform, a virtual machine instance executing on a server or some combination of the two. Various types and configurations of instances may be made available, including different sizes of resources executing different operating systems (OS) and/or hypervisors, and with various installed software applications, runtimes and the like. Instances may further be available in specific availability zones, representing a logical region, a fault tolerant region, a data center or other geographic location of the underlying computing hardware, for example. Instances may be copied within an availability zone or across availability zones to improve the redundancy of the instance, and instances may be migrated within a particular availability zone or across availability zones. As one example, the latency for client communications with a particular server in an availability zone may be less than the latency for client communications with a different server. As such, an instance may be migrated from the higher latency server to the lower latency server to improve the overall client experience.

In some embodiments the provider network may be organized into a plurality of geographical regions, and each region may include one or more availability zones. An availability zone (which may also be referred to as an availability container) in turn may comprise one or more distinct locations or data centers, configured in such a way that the resources in a given availability zone may be isolated or insulated from failures in other availability zones. That is, a failure in one availability zone may not be expected to result in a failure in any other availability zone. Thus, the availability profile of a resource instance is intended to be independent of the availability profile of a resource instance in a different availability zone. Clients may be able to protect their applications from failures at a single location by launching multiple application instances in respective availability zones. At the same time, in some implementations inexpensive and low latency network connectivity may be provided between resource instances that reside within the same geographical region (and network transmissions between resources of the same availability zone may be even faster).

A content provider may, for example, provide one or more content providing services for providing content to clients. The content providing services may reside on one or more servers. The content providing services may be scalable to meet the demands of one or more customers and may increase or decrease in capability based on the number and type of incoming client requests. Portions of content providing services may also be migrated to be placed in positions of reduced latency with requesting clients. The term content, as used herein, refers to any presentable information, and the term content item, as used herein, refers to any collection of any such presentable information. The term participant, as used herein, refers to any entity that participates in a presentation of a content item, such as a player that participates in a presentation of a video game.

As set forth above, a content item, such as a video game, may be managed according to various techniques disclosed herein. In particular, in some cases, a number of tasks may be selected for inclusion within a content item or content item portion. In some cases, tasks may be assigned to individual participants or to groups of participants, such as teams or factions. Also, in some cases, the same or similar tasks may be separately assigned to different individual participants and to different groups of participants.

Each task may be completed based, at least in part, on an associated set of one or more actions. The actions associated with a task may, for example, correspond to actions that may be performed by one or more participants as part of the task. In order to complete a task, a specified number of participants may, for example, be required to complete one or more action paths within the associated set of one or more actions. Some example action paths are described in detail below. In some cases, a set of one or more actions may include only a single action path that different participants are required to complete. However, in some other cases, a set of one or more actions may include multiple alternative action paths that different participants may complete. Also, in some cases, there may not be any requirement for one or more participants to complete any action paths. Rather, in some cases, a task may be completed based on an achievement of a specified level of progress associated with the task, without necessarily following or completing any particular action paths.

In some cases, a level of progress may be determined based, at least in part, on a particular number of completed actions. Also, in some cases, different actions may be assigned different weights, and a level of progress may be determined based on a combination of a number of completed actions and their associated weights. Furthermore, in some cases, one or more actions may be designated as mandatory actions that must be performed by one or more participants, while other actions may be designated as optional actions, of which, for example, only a certain number or percentage may need to be completed. It is noted, however, that even when a particular participant is not required to complete any particular actions paths, there may still be requirements for certain actions to be performed in some direct or indirect sequential relationship with respect to one another.

In addition to an associated set of one or more actions, a task may also be completed based, at least in part, on an associated set of one or more parameters. The parameters associated with a task may, for example, correspond to rules or other conditions associated with the task. Some example parameters may include an indication of various required action paths, required quantities of completed actions, weights associated with one or more actions, rules for calculating a required level of progress, mandatory and optional actions, sequential relationships between actions, a number of participants required to complete one or more actions or action paths, an allowed time within which to complete one or more actions or action paths, a level of difficulty and/or resistance associated with one or more actions, gameplay type, type of location or terrain (e.g., mountain, forest, town, water), specific region within an associated virtual geography (e.g., specific country or town), a preferred participant skill or experience level, assigned participants or groups of participants, a date and/or time range within which the task is available, various weapons or other features that may be employed in association with one or more actions and many others. In some cases, if the same or a similar task is separately assigned to different participants or to different groups of participants, then the required action paths and/or parameters may be different for each separately assigned task and may be tracked separately for each separately assigned task.

As should be appreciated, it is not required that all associated actions and/or parameters be specified for a task at the time that the task is selected for inclusion within a content item or content item portion. In some cases, any or all of the associated actions and/or parameters may be selected at any appropriate time after selection of the task itself. For example, in some cases, various associated actions and/or parameters may be selected after one or more participants have initiated playing of the content item or even after one or more participants have started to perform the task itself. Additionally, as set forth in detail below, the associated actions and/or parameters may also, in some cases, be adjusted at any appropriate time.

In some cases, information corresponding to content item characteristics may, for example, be collected before, during and/or after a playing of a content item. The content item characteristics may include any characteristics associated with a content item. The content item characteristics may include, for example, participant characteristics, task characteristics, various timing measurements and other characteristics associated with a content item. Participant characteristics may include, for example, participant quantity, participant skill level, participant preferences, participant interests, participant demographics, participant performance, participant progress, participant play style and the like. The task characteristics may include, for example, associated actions and parameters, a number of participants currently performing each task, a progress of completion, an elapsed time since initiation, a time limit, a preferred skill level, an associated play style, suggested demographics, a description, associated virtual geography, other associated requirements and the like. In some cases, the task characteristics for a task may indicate one or more other tasks whose availability is at least partially based upon a completion of the task. Also, in some cases, the task characteristics for a task may indicate one or more other tasks upon whose completion the availability of the task is at least partially based. The content item characteristics may be aggregated over various levels or combinations of levels, such as individual participants, teams, factions and other participant groups, all participants, individual actions, groups of actions, individual tasks, groups of tasks, story arcs, node layouts and others. As an example, in some cases, the content item characteristics may include action characteristics, which may include, for example, the above described task characteristics measured at the level of individual actions. The content item characteristic information may be collected and updated at any appropriate intervals.

The content item characteristic information may be collected using any combination of various techniques. For example, some content item characteristics may be collected by one or more content item manager components operated by a content provider and, in some cases, executing on one or more servers or other computing devices or environments. Content item characteristics may be collected based on, for example, information transmitted from content item participants operating one or more connected client computing devices. This may include, for example, state information associated with the content item as well as personal information associated with the participants themselves. In some cases, prior to joining a particular content item, participants may be asked to provide personal information that may describe, for example, their respective skill levels, play style, demographic information (e.g., age, gender, ethnicity, etc.) as well as their respective interests and preferences. Also, in some cases, participant characteristics may be determined and/or adjusted by software or algorithms based on an observed or collected history of participant behavior with respect to one or more content items. For example, if a participant consistently chooses to perform a sniper role in a number of different tasks, then it may be determined that the participant prefers to perform sniper roles. Some example preferences may include a preferred level of violence or action, a preferred time limit for gameplay, geographic areas of interest, subjects of interest, hobbies and the like. Content item characteristics may also be collected, for example, from other sources, such as files or code included within the content item itself, information from one or more content item developers or information from third parties or other associated entities.

In some cases, the collected content item characteristic information may be used to add, change and/or remove one or more tasks within a content item or content item portion. For example, in some cases, tasks may be added to a content item or content item portion by matching task characteristics to participant characteristics for participants associated with the content item or content item portion. For example, tasks may be added that may match interests, preferences, skill levels, play style, demographics and other characteristics of a participant or group of participants. Also, in some cases, if the participant characteristics change, then the tasks may be changed to match the change in player characteristics. Additionally, in some cases, tasks may be removed and new tasks may be selected to match a change in player characteristics.

Additionally, in some cases, the collected content item characteristic information may be used to add, change and/or remove one or more actions in a set of actions associated with a particular task. For example, in some cases, actions may be selected and added that have action characteristics that match participant characteristics for participants to which a task is assigned. For example, actions may be selected that may match interests, preferences, skill levels, play style, demographics and other characteristics of a participant or group of participants to which a task is assigned. Also, in some cases, if the participant characteristics change, then the actions may be changed to match the change in player characteristics. Additionally, in some cases, actions may be removed and new actions may be selected to match the change in player characteristics.

Furthermore, in some cases, the collected content item characteristic information may be used to add, change and/or remove one or more parameters in a set of parameters associated with a particular task. For example, in some cases, parameters may be selected and added based on a goal of having desired quantities and/or percentages of participants perform desired actions and tasks within desired time periods. Also, in some cases, if a task's associated participant characteristics change, then the parameters may be adjusted to match the change in player characteristics. Additionally, in some cases, parameters may be removed and new parameters may be selected to match the change in participant characteristics.

In some cases, one or more tasks within a content item or content item portion may be added, changed and/or removed based at least in part on various code or instructions associated with a content item. For example, such underlying code or instructions may describe various tasks available for use with the content item and their available associated features such as actions and parameters. Additionally, such underlying code or instructions may sometimes be used, at least in part, to add, change and/or remove actions in a set of actions and/or parameters in a set of parameters.

Figure 3A:
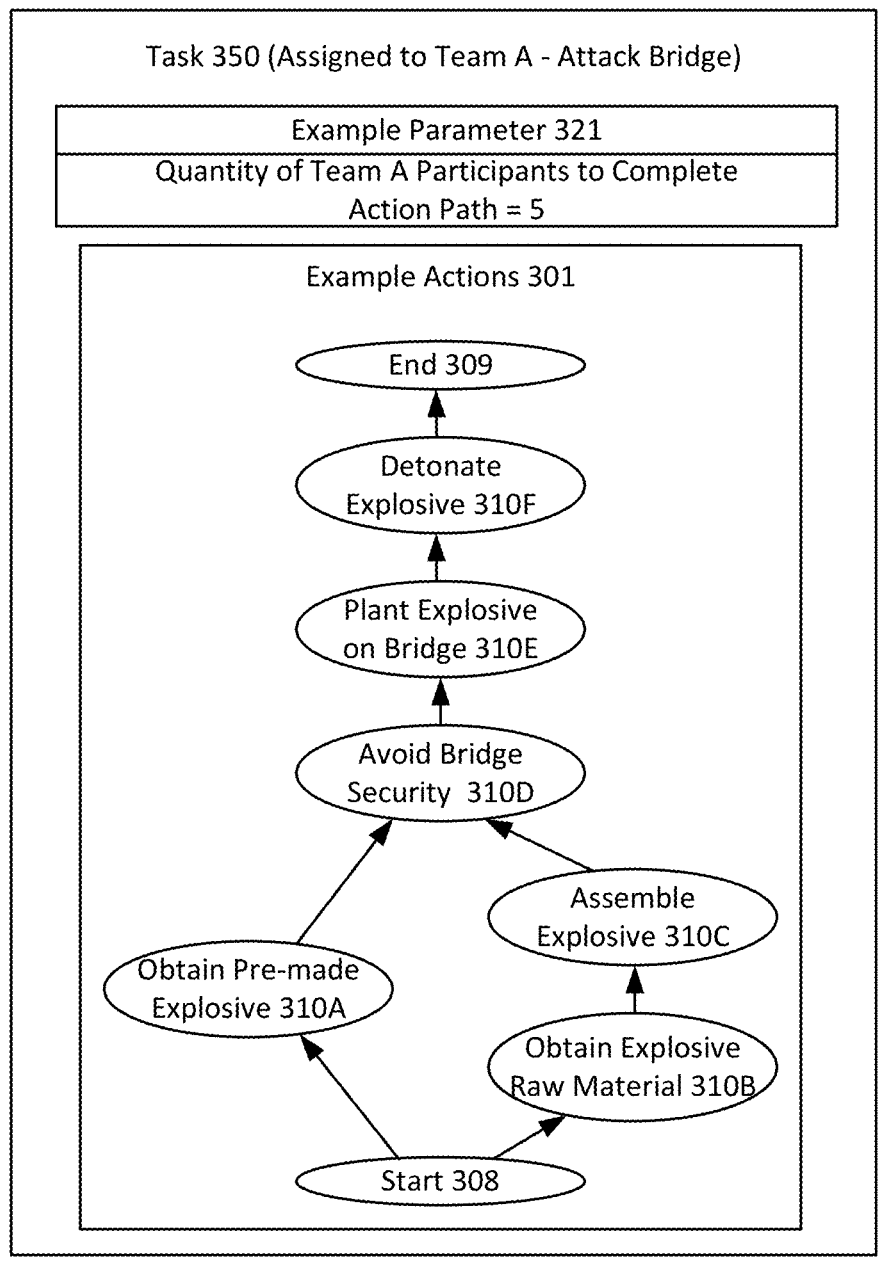
FIG. 3A is a diagram illustrating a first example of actions, parameters and content item characteristics associated with an example task.
Figure 3B:
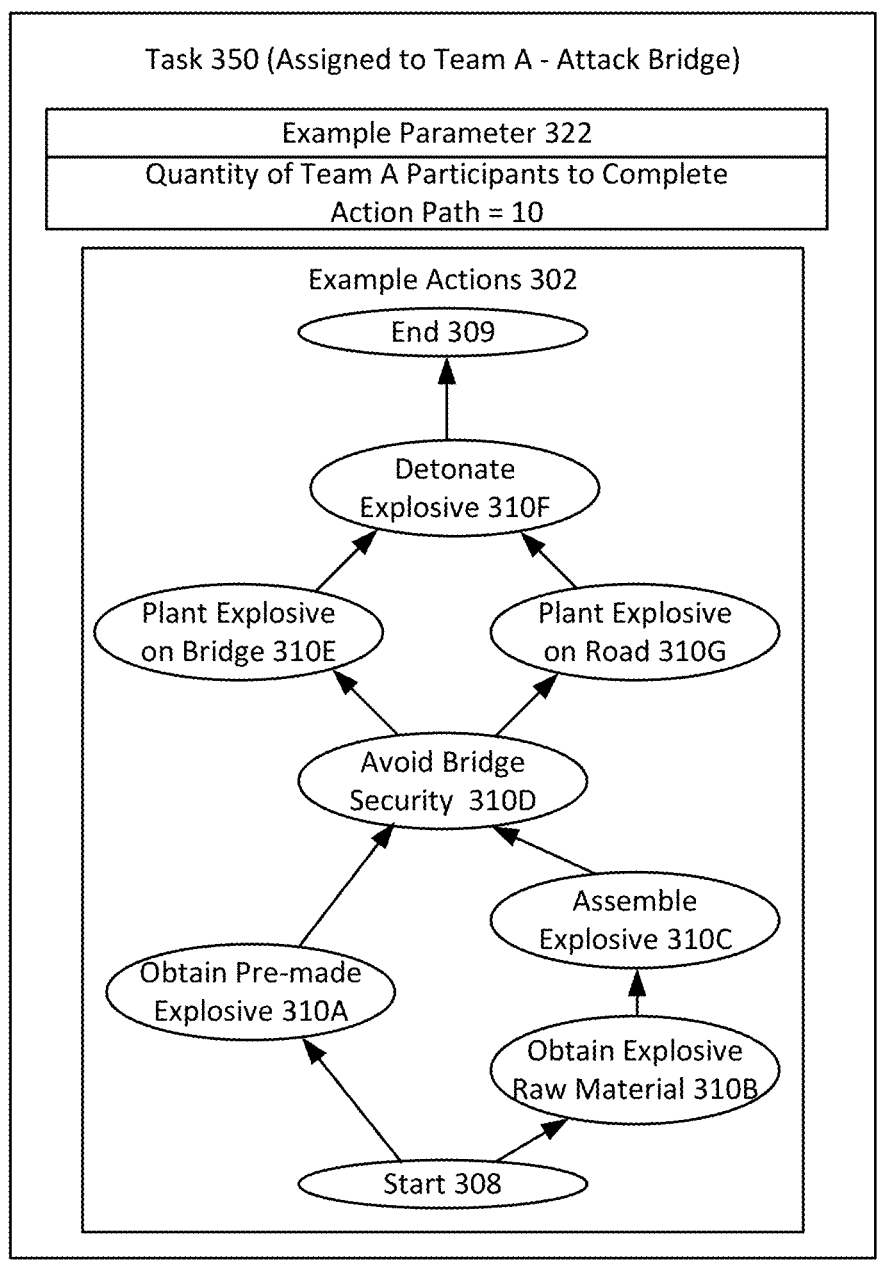
FIG. 3B is a diagram illustrating a first example adjustment of actions and parameters associated with an example task.

Some examples of how actions and/or parameters may be added, changed and/or removed in a set of actions and/or set of parameters associated with a task will now be described in detail. In particular, FIGS. 3A-3B depict an example of how actions and parameters may be selected and adjusted based on a quantity of participants. Specifically, FIG. 3A is a diagram illustrating a first example of information associated with an example task. As shown, FIG. 3A depicts example actions 301 and example parameter 321 that are associated with an example task 350. Task 350 is a task to attack a bridge, and, in the example of FIGS. 3A-3B, task 350 is assigned to Team A.

Example actions 301 include actions 310A-D and optionally additional actions not shown in FIG. 3A. In particular, action 310A is "Obtain Pre-made Explosives," action 310B is "Obtain Explosive Raw Material," action 310C is "Assemble Explosive," action 310D is "Avoid Bridge Security," action 310E is "Plant Explosive on Bridge" and action 310F is "Detonate Explosive". Example actions 301 include two alternative action paths from start 308 to end 309. The first action path branches from start 308 to the left to action 310A and includes actions 310A and 310D-F. The second action path branches from start 308 to the right to action 310B and includes actions 310B-F.

FIG. 3A includes an example content item characteristic 331, which indicates that there are 50 participants on Team A. FIG. 3A indicates that the example content item characteristic 331 is updated at Time T1. As should be appreciated, example content item characteristic 331 is merely one example content item characteristic, and any number of other additional or alternative content item characteristics not shown in FIG. 3A may also be collected.

FIG. 3A also includes an example parameter 321, which is "Quantity of Team A Participants to Complete Action Path=5." Parameter 321 indicates, in order to complete task 350, that 5 participants from Team A are required to complete one of the action paths shown in FIG. 3A. In some cases, certain participants may be specifically required to complete one of the two alternative action paths shown in FIG. 3A. As should be appreciated, example parameter 321 is merely one example parameter and any number of other additional or alternative parameters not shown in FIG. 3A may be included in a parameter set associated with task 350.

In some cases, a quantity of participants required to complete an action path may be selected based on, for example, a desired percentage of a total participants within a team with which a corresponding task is associated. For example, for the scenario depicted in FIG. 3A, it may be determined that it is desirable for ten percent of the participants on Team A to complete an action path associated with task 350. Thus, in such cases, parameter 321 may be set to a quantity of 5 participants because 5 is ten percent of the 50 total participants included in Team A (as indicated by characteristic 331). As should be appreciated, however there may be various other different factors or logic upon which a selection of parameter such as parameter 321 may be based.

Referring now to FIG. 3B, example content item characteristic 332 of FIG. 3B is updated at a time T2, which is subsequent to time T1. Additionally, example content item characteristic 332 of FIG. 3B indicates that, at time T2, there are 100 participants on Team A. Accordingly, the number of participants on Team A has doubled from time T1 to subsequent time T2. In some cases, it may be desirable to adjust a quantity of participants required to complete an action path such that, as the quantity of participants on a particular team changes, the percentage of participants required to complete an action path remains approximately constant. Thus, in FIG. 3B, example parameter 322 is adjusted such that the quantity of participants on Team A required to complete an action path is also doubled. In particular, parameter 322 of FIG. 3B, which requires 10 participants, is double the amount of parameter 321 of FIG. 3A, which required 5 participants. As should also be appreciated, parameter 322 (10 participants) continues to be equal to ten percent of characteristic 332 (100 participants). While FIG. 3B illustrates an example in which a constant percentage of participants completing an action path is maintained, it is noted that this is merely an example case and a constant percentage of participants may not necessarily be maintained in other examples.

In addition to changing the required number of participants completing an action path, there are other ways in which a task may be adjusted in response to a change in participant quantity. In particular, in FIG. 3B, in addition to changing the required number of participants completing an action path, the example actions 302 are adjusted in comparison to example actions 301 of FIG. 3A. Specifically, example actions 302 of FIG. 3B include an additional action 310G, which is "Plant Explosive on Road." The addition of action 310G results in four action paths being included within example actions 302. One action path includes actions 310A and 310D-F, another action path includes actions 310A, 310D, 310G and 310F, another action path includes actions 310B-F and another action path includes actions 310B-D, 310G and 310F.

There are a number of reasons why an increase in the quantity of participants on Team A may trigger the inclusion of additional action 310G in example actions 302. For example, the bridge that is being attacked in task 350 may not be large enough for more than approximately 5 participants to plant explosives on the bridge. Accordingly, the addition of action 310G creates an alternative whereby explosives are planted on a road adjacent to the bridge as opposed being planted on the bridge itself. In some cases, it may be assumed that approximately half the participants on Team A will choose to plant explosives on the bridge and that approximately the other half of participants on Team A will choose to plant explosives on the road. In some other cases, certain participants may be permitted to only plant explosives at one location or the other or may otherwise be influenced by the content item to plant explosives at one location or the other.

Figure 4A:
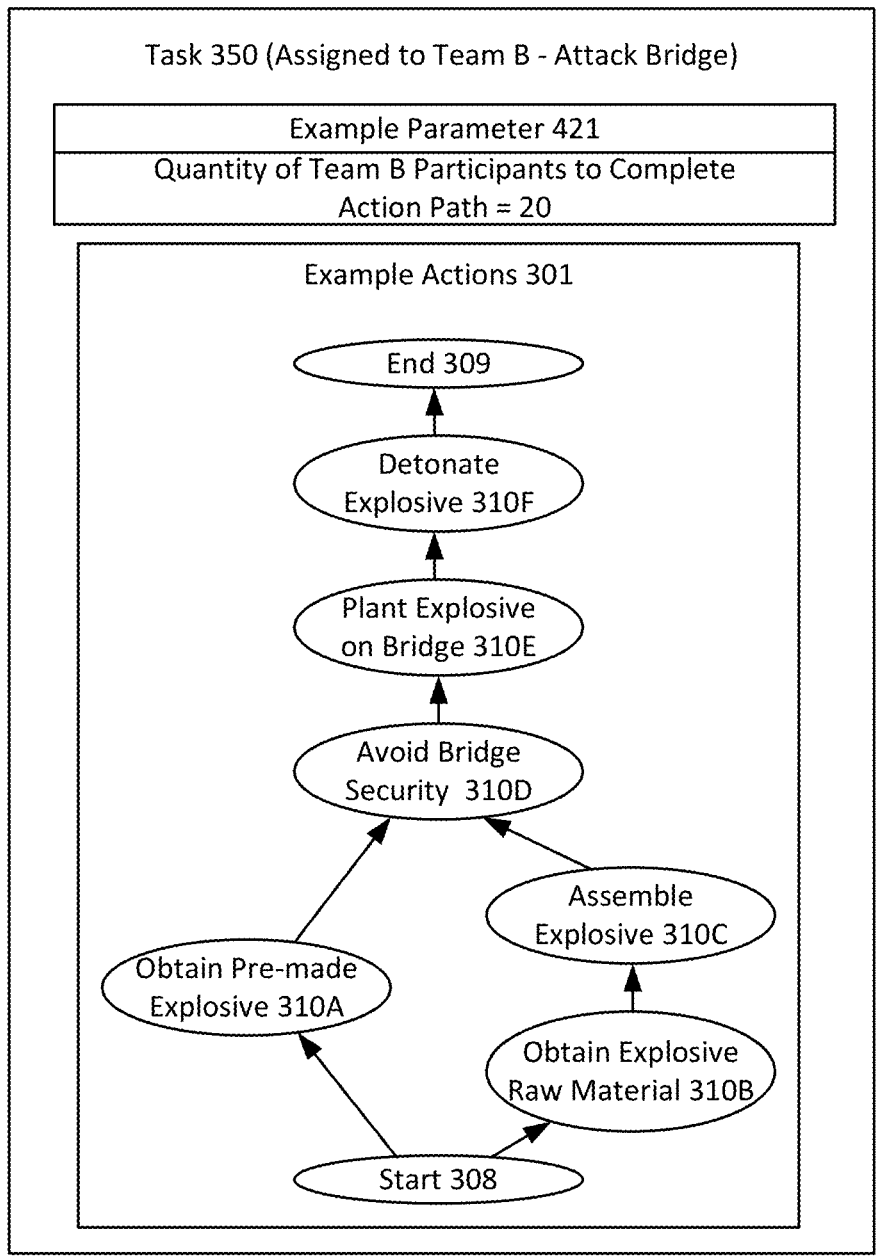
FIG. 4A is a diagram illustrating a second example of actions, parameters and content item characteristics associated with an example task.
Figure 4B:
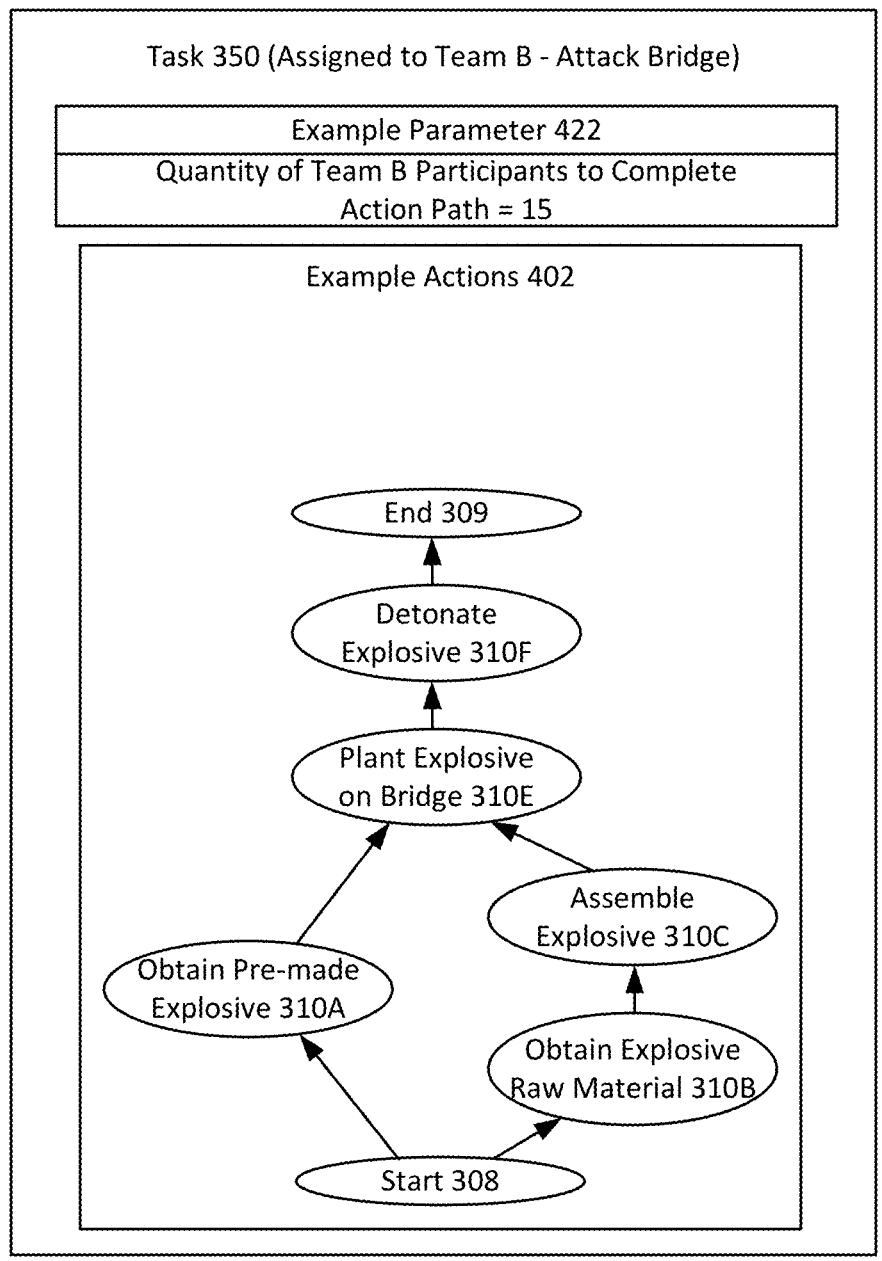
FIG. 4B is a diagram illustrating a second example adjustment of actions and parameters associated with an example task.

Thus, FIGS. 3A-3B show some examples of how actions and parameters may be selected and adjusted based on a quantity of participants. However, actions and parameters may also be selected and adjusted based on other characteristics. For example, FIGS. 4A-4B show some examples of how parameters may be selected and adjusted based on team performance. In particular, FIG. 4A once again shows task 350 with the same example actions 301 as were depicted previously in FIG. 3A. There are some differences, however, between FIG. 4A and prior FIG. 3A. Specifically, in the example of FIG. 4A, task 350 is assigned to Team B. Additionally, FIG. 4A includes an example parameter 421, which is "Quantity of Team B Participants to Complete Action Path=20." Parameter 421 indicates, in order to complete task 350, that 20 participants from Team B are required to complete one of the action paths shown in FIG. 4A.

FIG. 4A also includes example content item characteristic 431, which is updated at time TI. As shown in FIG. 4A, content item characteristic 431 is "Team B Performance Level=Higher." This performance level may, for example, indicate Team B's performance level with respect to other teams and/or Team B's performance level with respect to an estimated performance level. In particular, Team B may be competing against one or more other teams. For example, if Team B is outperforming other teams, then, in some cases, Team B's performance level may be considered to be higher. Team B may be considered to outperform other teams by, for example, completing more tasks and controlling more geographic areas and resources than other teams. By contrast, if Team B is underperforming other teams, then, in some cases, Team B's performance level may be considered to be lower. Team B may be considered to underperform other teams by, for example, completing fewer tasks and controlling fewer geographic areas and resources than other teams. As another example, if Team B has completed approximately the same amount of tasks and controls approximately the same geographic areas and/or resources as other teams, then, in some cases, Team B's performance level may be considered to be moderate.

In addition or as an alternative to being compared with other teams, Team B's performance level may also be based on an estimated performance level. For example, in some cases, Team B's performance level at a particular point in the content item may be estimated based on factors such as participant skill level, quantity of participants, elapsed time since a start of the content item or another point in the content item, started and completed tasks and many other factors. The estimated performance level may include, for example, an estimated amount of completed tasks and controlled geographic areas and resources. For example, in some cases, if Team B is outperforming the estimated performance level, then Team B's performance level may be considered to be higher. By contrast, in some cases, if Team B is underperforming the estimated performance level, then Team B's performance level may be considered to be lower. As another example, if Team B is approximately matching the estimated performance level, then, in some cases, Team B's performance level may be considered to be moderate.

Referring now to FIG. 4B, example content item characteristic 432 of FIG. 4B is updated at a time T2, which is subsequent to time T1. Additionally, example content item characteristic 432 of FIG. 4B indicates that, at time T2, Team B's performance level has decreased from higher to lower. As shown in FIG. 4B, in response to this change in Team B's performance level, the actions associated with task 350 are adjusted. In particular, FIG. 4B includes example actions 402, which are identical to example actions 301 of FIG. 4A with the exception that action 310D ("Avoid Bridge Security") is removed from example actions 402 of FIG. 4B. By removing action 310D ("Avoid Bridge Security") from the example actions 402, it is assumed, in some cases, that task 350 may be completed more quickly and more easily by the participants on Team B. Additionally, in some cases, allowing Team B to more easily complete task 350 may also improve the performance level of Team B. In some cases, in combination with removing action 310D, the content item may also be adjusted such that the bridge security is either eliminated or only minimally interferes with participants on team B as they perform task 350. Furthermore, FIG. 4B includes an example parameter 422, in which the quantity of participants from Team B required to complete an action path is reduced from 20 (as indicated in example parameter 421 of FIG. 4A) to 15. As should be appreciated, in some cases, reducing the number of participants required to complete an action path associated with a task may also allow the task to be completed more quickly.

It is noted that the example adjustments depicted in FIG. 4B are merely some examples of adjustments that may be made in response to a decrease in performance level. For example, in some other cases, a decrease in performance level may cause actions and parameters to be adjusted such that completion of tasks becomes more difficult instead of less difficult. For example, a decrease in performance level by a particular team may allow competing teams to acquire more resources that could be used against the particular team as it attempts to complete a task.

Figure 5A:
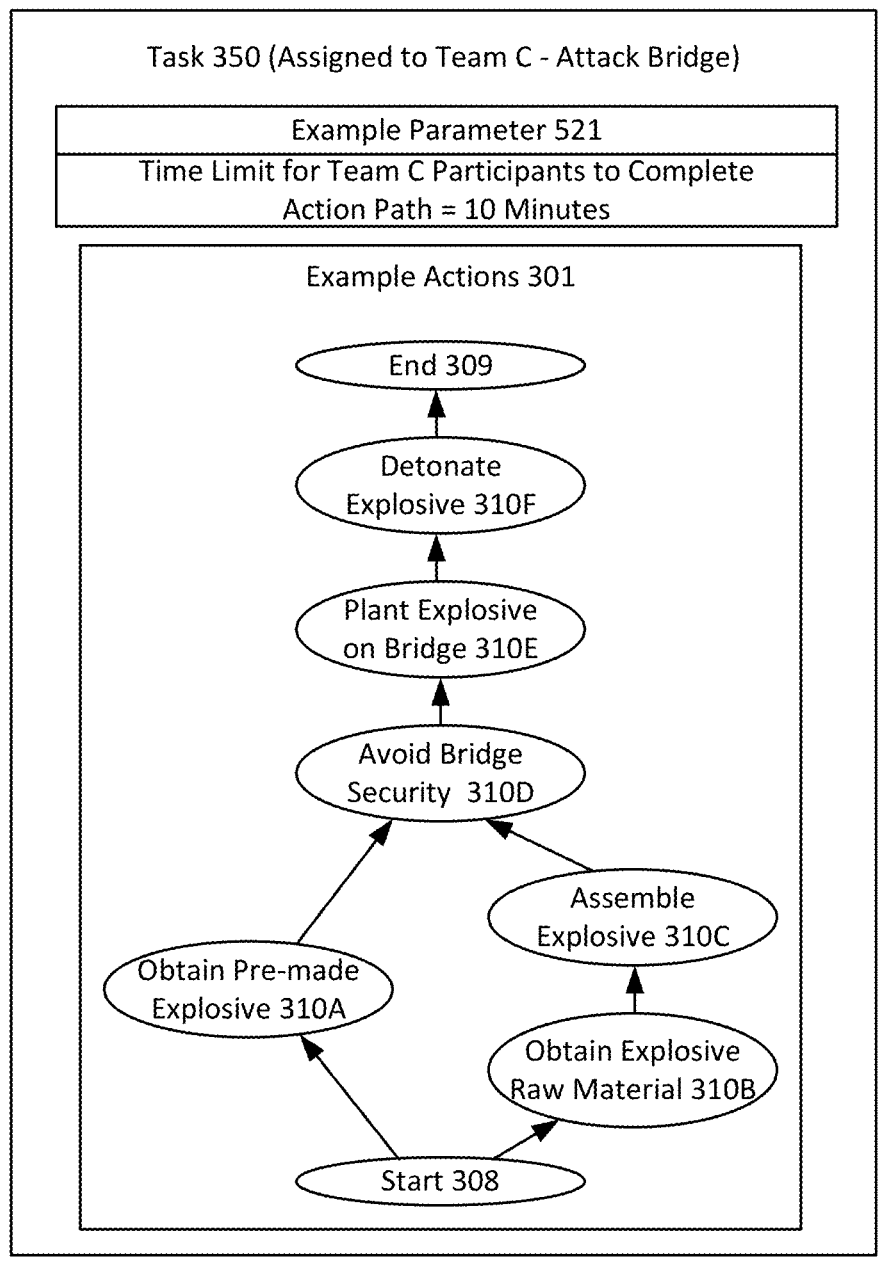
FIG. 5A is a diagram illustrating a third example of actions, parameters and content item characteristics associated with an example task.
Figure 5B:
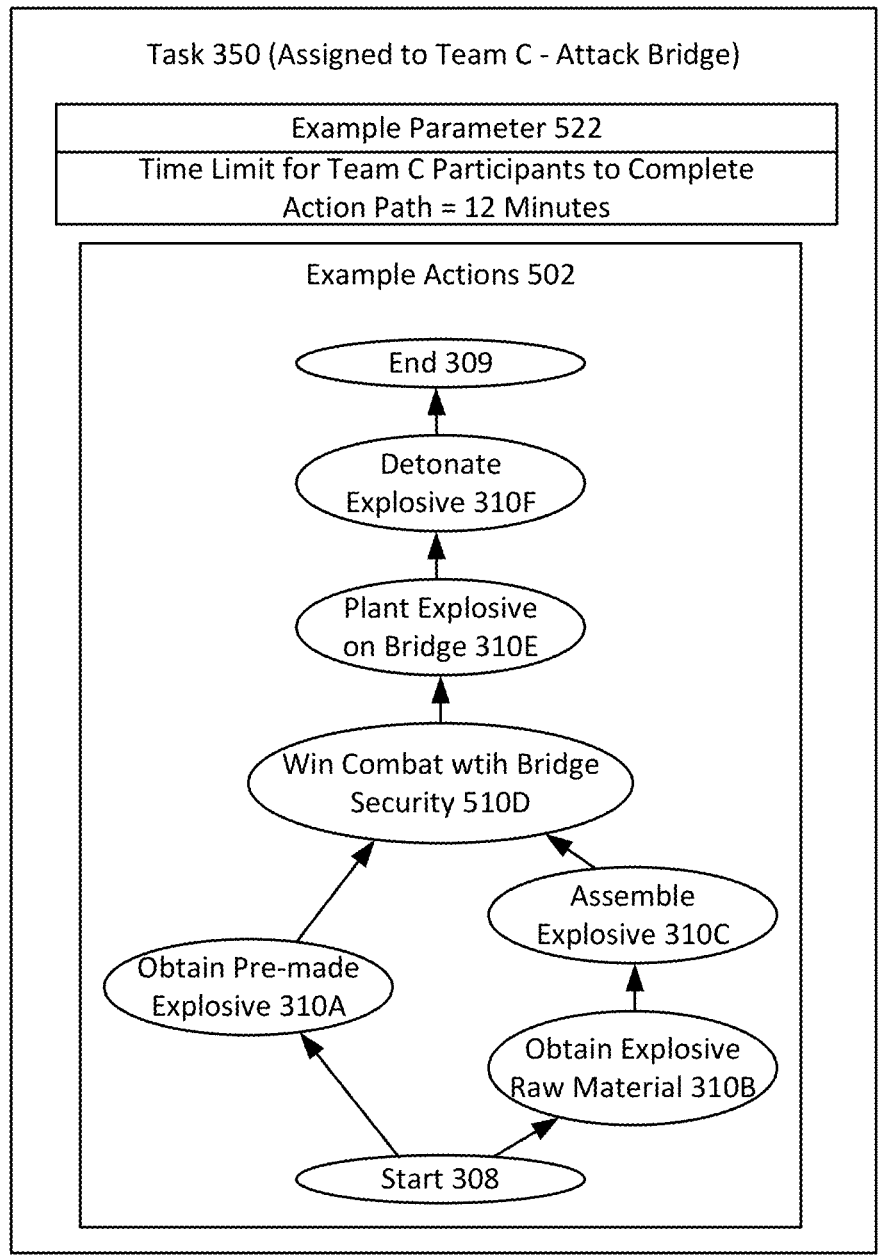
FIG. 5B is a diagram illustrating a third example adjustment of actions and parameters associated with an example task.

Thus, FIGS. 4A-4B show some examples of how actions and parameters may be adjusted based on a team performance level. However, actions and parameters may also be adjusted based on other characteristics. For example, FIGS. 5A-5B show some examples of how parameters may be adjusted based on participant preferences. In particular, FIG. 5A once again shows task 350 with the same example actions 301 as were depicted previously in FIGS. 3A and 4A. There are some differences, however, between FIG. 5A and prior FIGS. 3A and 4A. Specifically, in the example of FIG. 5A, task 350 is assigned to Team C. Additionally, FIG. 5A includes an example parameter 521, which is "Time Limit for Team C Participants to Complete Action Path=10 Minutes." Parameter 521 indicates that participants from Team C have a time limit of 10 minutes to complete one of the action paths within example actions 301. This time limit may, for example, be measured from a single particular start time or may be measured from a different start time for one or more different participants. For example, each participant's particular time limit may start from the time at which the participant enters a certain geographic area or from the occurrence of some other participant-specific event such as when the participant performs a first action in an action path.

FIG. 5A also includes example content item characteristic 531, which is updated at time TI. As shown in FIG. 5A, content item characteristic 531 is "Team C Participant Preferences=Lower Level of Violence." Content item characteristic 531 indicates that the participants on Team C prefer a lower level of violence within the content item. As set forth above, participant preferences may be determined based on, for example, personal information provided by each participant as they join the content item. As different participants join and leave the content item, the participants that are included within Team C may change over time, and, accordingly, the participant preferences associated with Team C may also change over time. As should be appreciated, violence level is merely intended to be one example type of participant preference and many other participant preferences may be included, such as preferred terrain (e.g., beach, mountains, city), preferred time window for content item completion, preferred level of resistance, preferred gender of characters, preferred weapons, preferred obstacles and many others.

Referring now to FIG. 5B, example content item characteristic 532 of FIG. 5B is updated at a time T2, which is subsequent to time T1. Additionally, example content item characteristic 532 of FIG. 5B indicates that, at time T2, Team C's preference has changed from a lower level of violence (as indicated in characteristic 531 of FIG. 5A) to a higher level of violence (as indicated in characteristic 532 of FIG. 5B). As shown in FIG. 5B, in response to this change in Team C's preferences, the actions associated with task 350 are adjusted. In particular, FIG. 5B includes example actions 502, which are identical to example actions 301 of FIG. 5A with the exception that action 310D ("Avoid Bridge Security") is removed from example actions 502 of FIG. 5B and replaced in FIG. 5B with action 510D ("Win Combat with Bridge Security"). It is assumed that the action 510D ("Win Combat with Bridge Security") may be more appropriate than action 310D ("Avoid Bridge Security") for participants that prefer a higher level of violence within the content item. By contrast, it is assumed that that the action 310D ("Avoid Bridge Security") may be more appropriate than action 510D ("Win Combat with Bridge Security") for participants that prefer a lower level of violence within the content item. Furthermore, FIG. 5B includes an example parameter 522, in which the time limit for completing an action path is increased from 10 minutes (as indicated in example parameter 521 of FIG. 5A) to 12 minutes. As should be appreciated, in some cases, it is expected that it may take longer to win combat with bridge security (as depicted in FIG. 5B) than to simply avoid bridge security (as depicted in FIG. 5A). Accordingly, in FIG. 5B, the time limit for completing an action path is increased to allow more time for winning combat with bridge security (as depicted in FIG. 5B).

In some cases, the parameters associated with a task may include various participant roles that may be employed in connection with the task. For example, a task that involves attacking an enemy base may include roles such as snipers, scouts, hand-to-hand combat participants, tank operators, pilots and the like. In some cases, each of the associated roles may be assigned to one or more participants. Each of the roles may, for example, have their own associated actions or action paths for completion by the participants to whom the roles are assigned. Each of the roles may also have their own associated parameters, such as a number or percentage of participants on a team to which each role will be assigned. In some cases, the roles and their associated actions and parameters may be selected and adjusted based on one or more content item characteristics. For example, if a greater than expected number of enemy troops are deployed to defend an enemy base, then an increased quantity of snipers may be required to attempt to eliminate the enemy troops.

Accordingly, as set forth above, one or more tasks and one or more associated actions and parameters may be selected and adjusted based, at least in part, on content item characteristics. In some cases, one or more selected tasks, such as example task 350 described above, may each be associated with a node in a node layout such as a graph or another collection of data or construct. For example, data may be generated in accordance with one or more node layouts to represent a particular content item or portions of a content item such as different story arcs.

Each node within a node layout may, for example, have at least one associated task within a respective content item or content item portion. The node layout may, for example, at least partially indicate one or more relationships between two or more nodes within the node layout. A relationship between nodes may be based on, for example, virtual geography corresponding to tasks associated with various nodes. A relationship between nodes may also be based on, for example, an availability of a task associated with one node being based, at least in part, on a completion of one or more other tasks associated with one or more other nodes. A node layout is a construct that includes a plurality of nodes corresponding to a content item or content item portion. A node layout may, for example, be a graph or be represented using a graph. However, there is no requirement that a node layout be a graph or be represented using a graph. For example, in some cases, a node layout may simply be a collection of data or other construct.

A content item may, for example, have one or more associated node layouts, each corresponding to one or more particular story arcs and to one or more participants or groups of participants. In some examples, one or more node layouts may be generated for a content item in which participants may interact with each other directly in a consistent world, such as may occur, for example, in an MMO game. In some other examples, participants may have separate or partially separate experiences that are influenced by each other, such as may occur, for example, with disconnected or partially disconnected characters that share a similar story world with similar major events. In some cases, one or more content item designers may create an overall story arc, and provide initial information describing what happens during the arc, such as how long the arc should last, quantities and other characteristics of included tasks, quantities and other characteristics of participants involved and the like. The content item designers may include, for example, human content item designers and/or software component content item designers. In some cases, there may be multiple simultaneous story arcs that influence one another, and an arc may branch based on factors such as participant choices or performance.

In some cases, based on factors such as a designed story arc, one or more associated tasks and one or more content item characteristics as described above, a node layout may be generated to represent a content item or content item portion. A node layout may sometimes be generated at a higher level during an initialization step, while lower level details of the node layout may be filled in as content item play progresses through the content item or content item portion. For example, in some cases, a node layout generated at a higher level may include various nodes that are reserved for tasks that have not yet been specified. The tasks associated with these nodes may then be specified at a later time after playing of the content item or content item portion has been initiated. In some cases, the amount of story progress per completed task may be tuned dynamically and/or automatically, so that participants progress towards the end of the story with a desired velocity.

Figure 6:
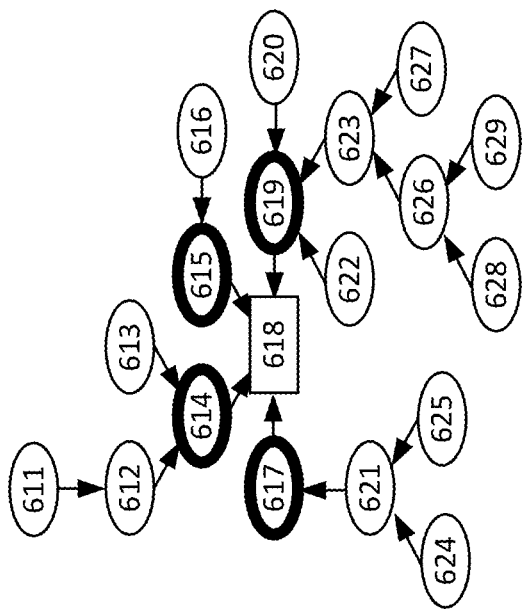
FIG. 6 is a diagram illustrating a first example node layout.

FIG. 6 is a diagram illustrating an example node layout. As shown, node layout 600 includes nodes 611-629. In the particular example of FIG. 6, each such node 611-629 corresponds to a respective task. As also set forth above, node layout 600 may, for example, correspond to one or more particular story arcs and may correspond to one or more participants, teams or other groups of participants. As should be appreciated, node layout 600 is in the form of a node graph. However, there is no requirement that a node layout must be a graph. For example, as set forth above, a node layout may be a collection of data or other construct.

Various techniques for determining when a task is completed are set forth in detail above. One such example technique includes determining that a specified quantity of participants has completed an action path associated with the task. In some cases, a node layout and/or associated data may indicate which nodes within the node layout correspond to tasks that are completed and that have yet to be completed. For example, in node layout 600, each node associated with a completed task is indicated with a rectangular shape, while each node associated with an uncompleted task is indicated with an ovular shape. As shown in FIG. 6, only a single node 618 is associated with a completed task, while the remaining nodes 611-617 and 619-629 are associated with uncompleted tasks. For purposes of simplicity, nodes that are associated with completed tasks are referred to herein as completed nodes, while nodes that are associated with uncompleted tasks are referred to herein as uncompleted nodes. FIG. 6 includes a box 605 that lists completed nodes in node layout 600 (including node 618) and a box 606 that lists the uncompleted nodes in node layout 600 (including nodes 611-617 and 619-629).

In some cases, one or more tasks associated with nodes in a node layout may be designated as being either available or unavailable. There are a number of factors that may cause a task to be designated as being either available or unavailable. For example, in some cases, the availability of one or more tasks may be at least partially based on a completion of one or more other tasks. This may occur, for example, when tasks are associated with respective geographic areas. For example, an availability of a task associated with a particular geographic area may be at least partially based on a completion of at least one other task that results in control of at least one neighboring geographic area. As another example, in some cases, a particular task may require the use of one or more resources that are acquired as a result of a completion of one or more other tasks. For example, a particular task may require the use of a special weapon or key that is acquired as a result of a completion of one or more other tasks. In these and other cases, an availability of a particular task may be at least partially based on a completion of one or more other tasks. Furthermore, in some cases, other factors may be involved in designating a particular task as being either available or unavailable. For example, the availability of some tasks may be at least partially based on factors such as a minimum and/or maximum quantity of participants, a minimum and/or maximum participant skill level, various participant preferences, an elapsed time limit from the start of the content item or another point within the content item.

In some cases, a node layout and/or associated data may indicate which nodes within the node layout are associated with tasks that are available or unavailable. For example, in node layout 600, each node associated with an available task is shown with bolder (i.e., thicker) outlining, while each node associated with an unavailable task is shown with thinner outlining. As shown in FIG. 6, nodes 614, 615, 617 and 619 are associated with available tasks, while nodes 611-613, 616, 618 and 620-629 are associated with unavailable tasks. For purposes of simplicity, nodes that are associated with available tasks are referred to herein as available nodes, while nodes that are associated with unavailable tasks are referred to herein as unavailable nodes. FIG. 6 includes a box 601 that lists the available nodes in node layout 600 (including nodes 614, 615, 617 and 619) and a box 602 that lists the unavailable nodes in node layout 600 (including nodes 611-613, 616, 618 and 620-629).

Figure 7:
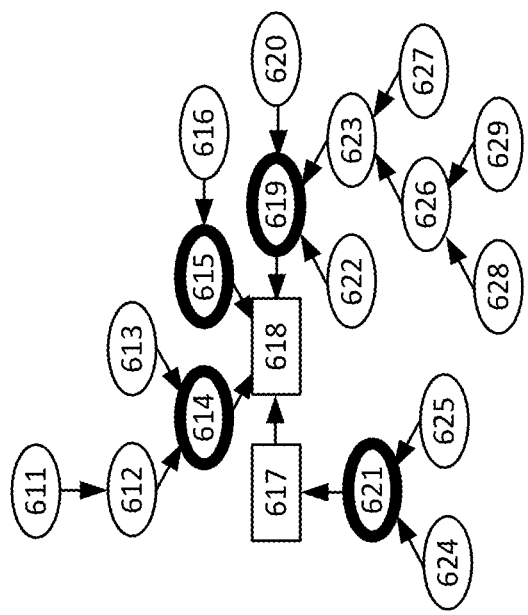
FIG. 7 is a diagram illustrating a second example node layout.

In some cases, a node layout and/or associated data may indicate when an availability of a task associated with a particular node is at least partially based on a completion of one or more other tasks associated with one or more other nodes. For example, the arrows pointing from node 621 to node 617 may indicate that the availability of the task associated with node 621 is at least partially based on a completion of the task associated with node 617. For example, referring now to FIG. 7, it is seen that FIG. 7 depicts a node layout 700. Node layout 700 of FIG. 7 is identical to node layout 600 of FIG. 7 with the exceptions that, in node layout 700, node 617 has changed from an oval to a square and node 621 has changed from a thinner outline to a thicker outline. Thus, node layout 700 represents the scenario in which the task associated with node 617 is completed. Additionally, the task associated with node 621 has responsively become available, at least in part, due to the completion of the task associated with node 617.

A node layout and/or associated data may, for example, at least partially indicate one or more relationships between two or more nodes within the node layout. A relationship between nodes may be based on, for example, virtual geography corresponding to tasks associated with various nodes. For example, the node layout and/or associated data may sometimes indicate which nodes are associated with tasks that correspond to geographic areas that are adjacent to one another in a virtual geography associated with the content item. A relationship between nodes may also be based on, for example, an availability of a task associated with one node being based, at least in part, on a completion of one or more other tasks associated with one or more other nodes. As set forth above, these types of relationships may be based on factors such as virtual geography, weapons, resources and various other factors.

Each node of a node layout may, for example, have at least one associated task within the at least portion of the video game. In some cases, each node may include or otherwise be associated with data corresponding to the at least one associated task. This data may include, for example, a task title, a task identifier, associated actions and parameters, indications of relationships to one or more other nodes, indications of whether an associated task is available or unavailable, timing measurements, indications of whether an associated task is completed or uncompleted, associated content item characteristics such as task and/or action characteristics, participant characteristics and various other characteristics and data. When a task and/or its associated actions and parameters are changed, an associated node and/or associated data may also be changed to reflect the changes to the task, actions and/or parameters.

A node layout and/or associated data may also be used to track and/or to represent the progress of a respective content item and/or content item portion corresponding to the node layout. For example, in some cases, when the content item and/or content item portion is initiated, each of the nodes in the node layout may indicate that their associated tasks are not yet completed. As the content item and/or content item portion progresses, the nodes may gradually change from an indication of an uncompleted task to indication of a completed task. Finally, in some cases, when all nodes in the node layout indicate that their respective tasks are complete, the respective content item and/or content item portion may also be considered to be completed. In these and other cases, a node layout and its included nodes may sometimes be used to indicate a percentage of ownership that a respective participant or team has acquired with respect to a story arc or other content item or content item portion to which the node layout corresponds.

A node layout and/or associated data may also be used to assign participants to one or more tasks. For example, a task scheduler may sometimes be employed to examine a node layout and/or associated data and to assign participants to tasks based at least in part on the node layout and/or associated data. In particular, in some cases, at the initiation of a content item or content item portion corresponding to the node layout, participants may be assigned to one or more tasks that are indicated by the node layout as being available tasks. As participants complete their assigned tasks, they may then be reassigned to other tasks that are indicated by the node layout and/or associated data as being available tasks. Additionally, as new participants join the content item, the new participants may also be assigned to one or more tasks that are indicated by the node layout and/or associated data as being available tasks. In some cases, participants may be assigned to tasks based at least in part on a comparison of participant characteristics associated with the participant to task characteristics for one or more available tasks. The participant may then, for example, be assigned to a task that is determined to have task characteristics that match the participant characteristics of the participant. In some cases, in addition to individual participants, characteristics for teams or other groups of participants or even for all active participants may be compared to one or more task characteristics. Also, in some cases, characteristics of even some presently unavailable tasks may be considered, for example, in anticipation of their eventual availability.

It should be appreciated that node layouts 600 and 700 are merely some example node layouts that may be employed in accordance with the disclosed techniques. For example, while FIGS. 6 and 7 represent scenarios in which each node in a node layout corresponds to a single associated task, there may be other scenarios in which one or more nodes in a node layout correspond to multiple associated tasks. As another example, in some cases, a node layout or portions of a node layout may be acyclic, while, in some other cases, a node layout or portions of a node layout may be cyclic. As another example, in some cases, a node layout or portions of a node layout may include directed dependencies between nodes, while, in some other cases, a node layout or portions of a node layout may not include directed dependencies between nodes. As yet another example, in some cases, a node layout or portions a node layout may include one or more start nodes and/or one or more end nodes, while, in some other cases, a node layout or portions of a node layout may not include one or more start nodes and/or one or more end nodes. Furthermore, in some cases, a content item and/or content item portion may be configured to run indefinitely and/or to run at least temporarily without a defined end point. Accordingly, in some cases, node layouts may also be configured to extend indefinitely and/or at least temporarily without a clearly defined end point. Also, in some cases, one or more nodes within a particular node layout may cross-over into, or otherwise be associated with, nodes in another node layout. This may occur, for example, when participants on multiple different teams are performing the same or similar tasks associated with the nodes that cross-over between node layouts. In some cases, participants on different teams may perform these tasks with different roles and with different associated parameters and/or actions.

In some cases, one or more nodes in a node layout may be adjusted based on, for example, content item characteristics. Content item characteristics are described in detail above and this description is not repeated here. As a specific example, in some cases, when a team is not completing tasks as quickly as expected, the team's performance level may be considered to be lower. In such cases, one or more nodes may sometimes be removed from a node layout associated with the team. Removal of nodes from the node layout may, for example, reduce the amount of tasks that the team is required to complete in order to complete an associated story arc within the content item. This reduction of tasks may, in some cases, help to offset the slow progress of the team and allow the team to complete the associated story arc within a desired time period.

Figure 8A:
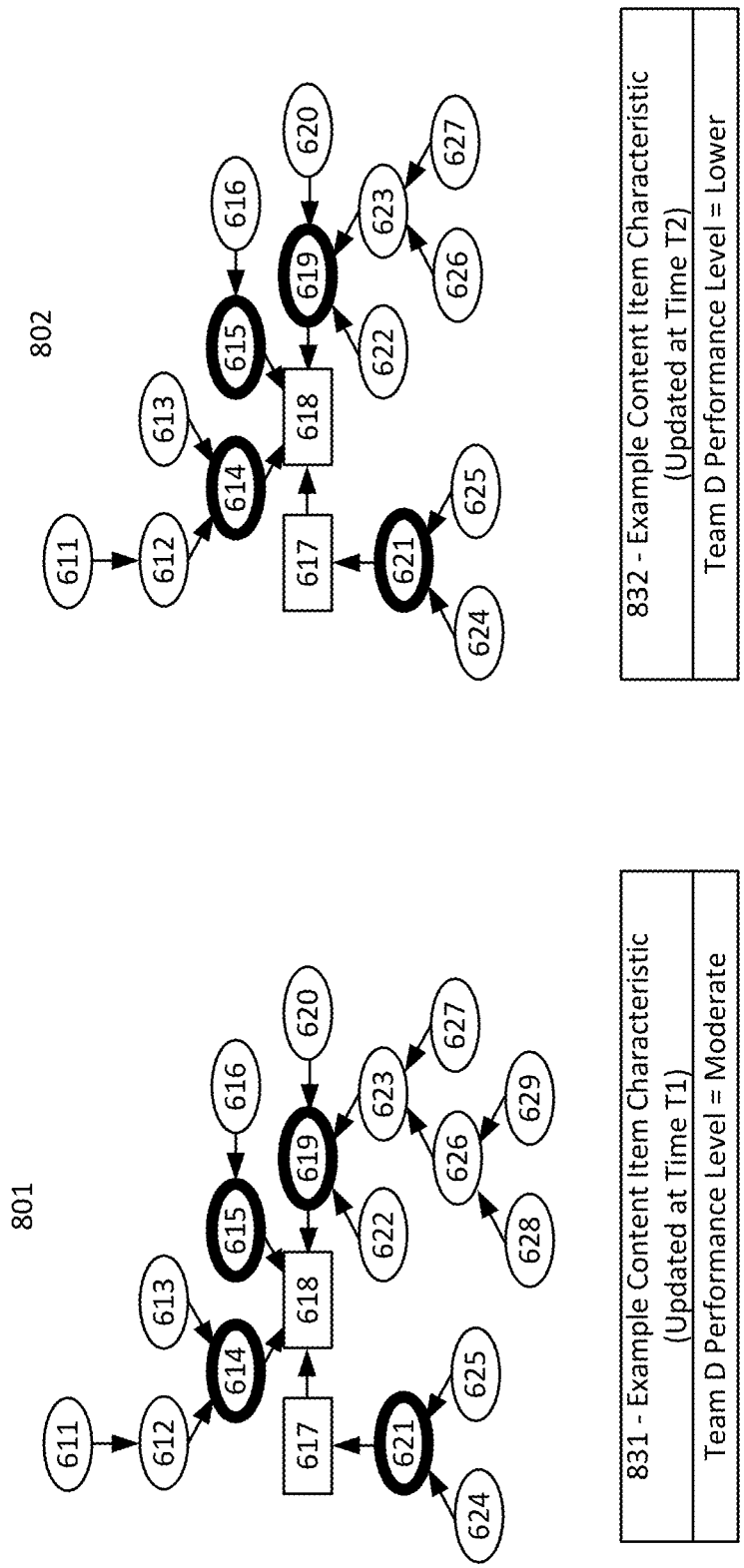
FIG. 8A is a diagram illustrating a first example adjustment to a node layout.

An example of the adjustment described above is depicted in FIG. 8A. Specifically, FIG. 8A includes an example content item characteristic 831 that is updated at Time T1. The video example content item characteristic 831 is "Team D Performance Level=Moderate." This indicates that, at Time T1, Team D's performance level within its associated story arc is moderate. As set forth above, a moderate performance level may indicate, in some cases, that Team D is completing tasks approximately as quickly as expected. Adjacent to example content item characteristic 831 is shown a first node layout 801 that represents Team D's story arc at time T1. Additionally, FIG. 8A includes an example content item characteristic 832 that is updated at Time T2, which is subsequent to Time T1. The example content item characteristic 832 is "Team D Performance Level=Lower." This indicates that, at time T2, Team D's performance level has decreased from moderate to lower. As set forth above, this decrease in performance level may be due to, for example, Team D not completing tasks as quickly as expected. Adjacent to example content item characteristic 832 is shown a second node layout 802 that represents Team D's story arc at time T2. As shown in FIG. 8A, Team D's node layout has been adjusted based on Team D's decrease in performance from Time T1 to Time T2. In particular, by comparing node layouts 801 and 802, it can be seen that two nodes (nodes 628 and 629) that were included in node layout 801 have been removed from node layout 802. As set forth above, removing of nodes from the node layout 802 may, for example, reduce the amount of tasks that Team D is required to complete, which may enable Team D to complete its associated story arc within a desired time period.

It is noted that, in addition to removing nodes, a node layout may also be adjusted in other ways to help offset lower than expected performance by a team. For example, an unavailable node, whose availability is dependent upon the completion of other uncompleted nodes, may sometimes be rearranged within the node layout such that its availability is no longer dependent upon the completion of other uncompleted nodes. This may cause the rearranged node to become available. This may have the effect of increasing a quantity of tasks that can be performed in parallel by participants on a team. By allowing participants on a team to perform a greater quantity of tasks in parallel, the team may sometimes be able to complete more tasks within a shorter time period.

As another specific example, in some cases, when a team is completing tasks more quickly than expected, the team's performance level may be considered to be higher. In such cases, one or more nodes may sometimes be added to a node layout associated with the team. Adding of nodes to the node layout may, for example, increase the amount of tasks that the team is required to complete in order to complete an associated story arc within the content item. This increase of tasks may, in some cases, help to offset the fast progress of the team and help prevent the team from completing an associated story too quickly.

Figure 8B:
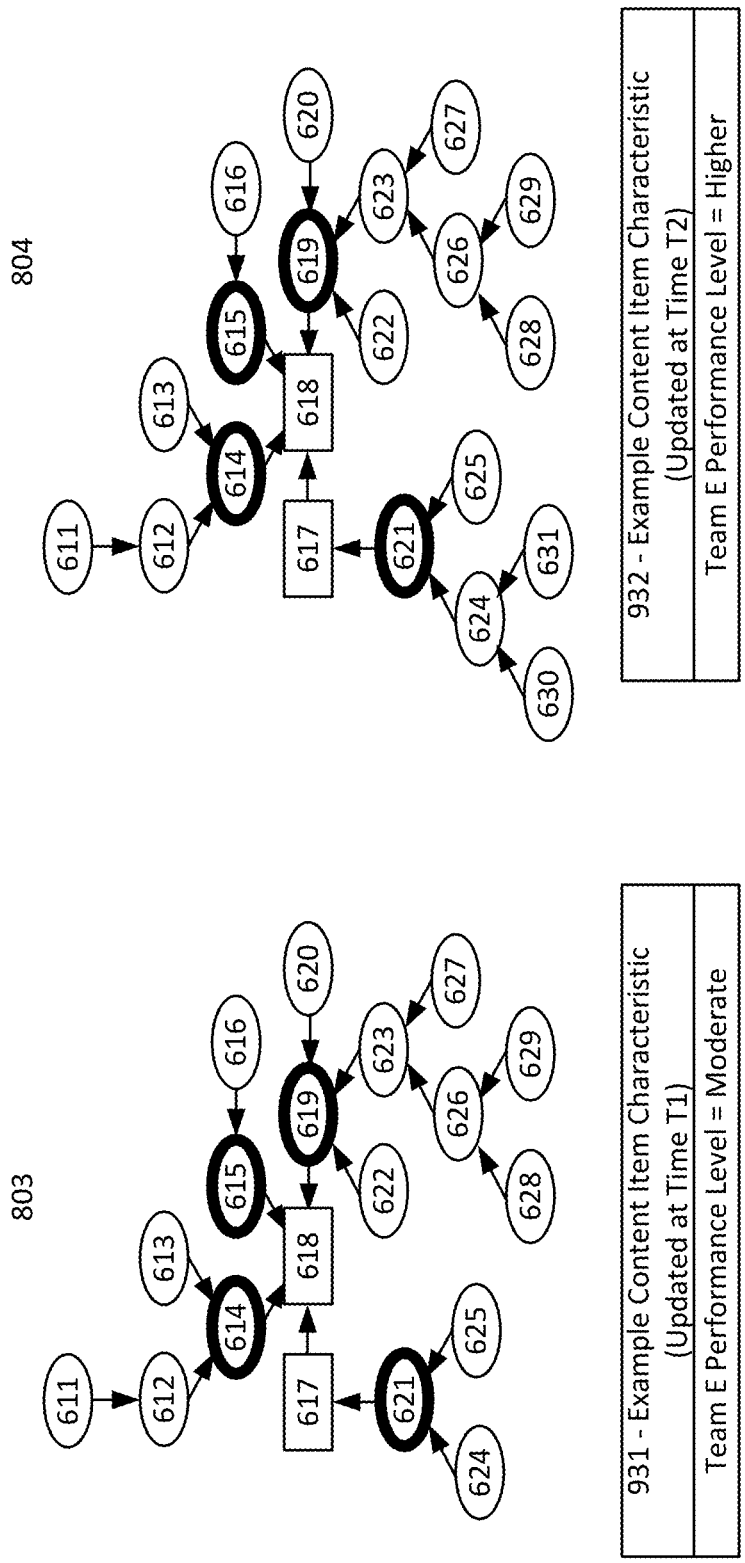
FIG. 8B is a diagram illustrating a second example adjustment to a node layout.

An example of the adjustment described above is depicted in FIG. 8B. Specifically, FIG. 8B includes an example content item characteristic 931 that is updated at Time T1. The video example content item characteristic 931 is "Team E Performance Level=Moderate." This indicates that, at Time T1, Team E's performance level within its associated story arc is moderate. As set forth above, a moderate performance level may indicate, in some cases, that Team E is completing tasks approximately as quickly as expected. Adjacent to example content item characteristic 931 is shown a first node layout 803 that represents Team E's story arc at time T1. Additionally, FIG. 8B includes an example content item characteristic 932 that is updated at Time T2, which is subsequent to Time T1. The example content item characteristic 932 is "Team E Performance Level=Higher." This indicates that, at time T2, Team E's performance level has changed from moderate to higher. As set forth above, this increase in performance level may be due to, for example, Team E completing tasks more quickly than expected. Adjacent to example content item characteristic 932 is shown a second node layout 804 that represents Team E's story arc at time T2. As shown in FIG. 8B, Team E's node layout has been adjusted based on Team E's increase in performance from Time T1 to Time T2. In particular, by comparing node layouts 803 and 804, it can be seen that two nodes (nodes 630 and 631) that are not included in node layout 803 have been added to node layout 804. As set forth above, adding of nodes to node layout 804 may, for example, increase the amount of tasks that Team E is required to complete, which may prevent Team E from completing an associated story too quickly.

It is noted that, in addition to adding nodes, a node layout may also be adjusted in other ways to help offset higher than expected performance by a team. For example, an available node may sometimes be rearranged within the node layout such that its availability becomes dependent upon the completion of other uncompleted nodes. This may cause the rearranged node to become at least temporarily unavailable until the tasks associated with the other nodes are completed. This may have the effect of decreasing a quantity of tasks that can be performed in parallel by participants on a team. By allowing participants on a team to be perform a lower quantity of tasks in parallel, the team may sometimes require a longer time period in order to complete tasks in a story arc.

Figure 9A:
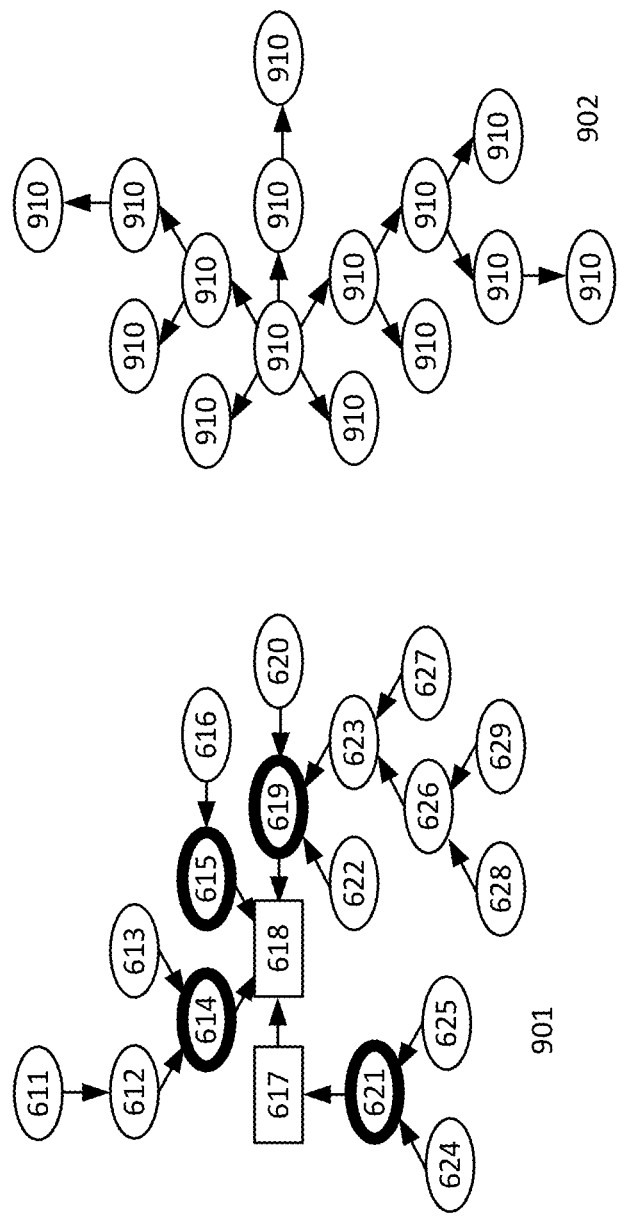
FIG. 9A is a diagram illustrating two separate node layouts.
Figure 9B:
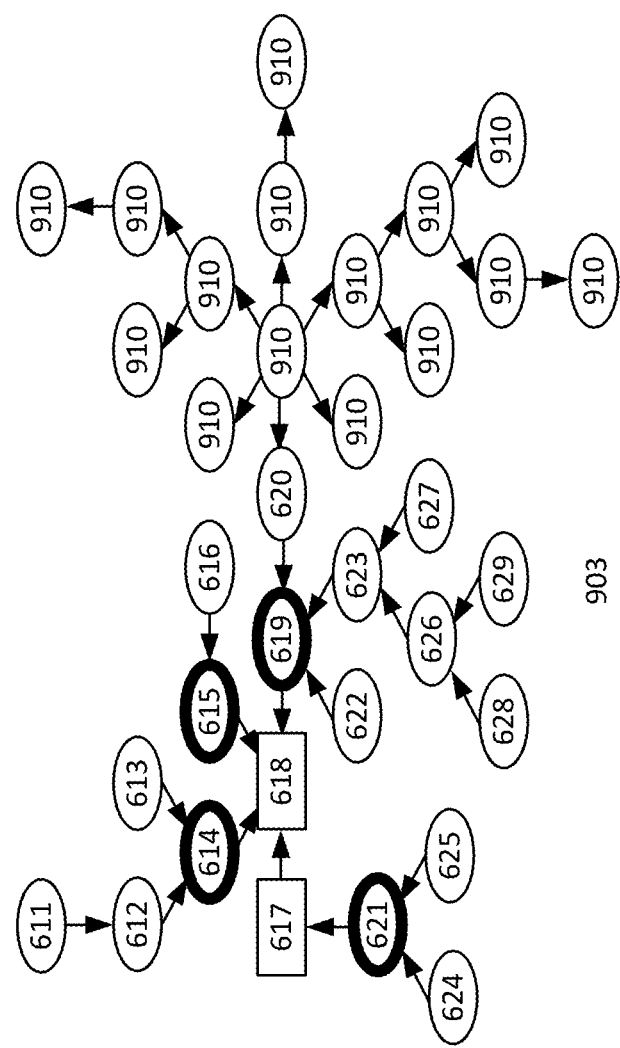
FIG. 9B is a diagram illustrating a combination of two separate node layouts.

Thus, some examples of addition, subtraction and rearrangement of nodes in a node layout are set forth above. Additionally, in some cases, multiple different node layouts may be wholly or partially combined with one another. For example, FIG. 9A depicts two separate node layouts 901 (including nodes 611-629) and 902 (including nodes 910). Referring now to FIG. 9B, it can be seen that node layouts 901 and 902 have combined into a single node layout 903. This may occur, for example, when a task leads into a node layout associated with another story arc. This may also occur, for example, when participants or teams with separate story arcs join forces and work together in a shared story arc. As should also be appreciated, in some cases, a single node layout may be divided into multiple different node layouts. For example, node layout 903 of FIG. 9B could be divided node layouts 901 and 902 of FIG. 9A. This may also occur, for example, when participants on a team choose to follow separate story arcs. It is noted, however, that even when participating in separate story arcs, the participants may sometimes continue to work together towards a common goal and may eventually rejoin into a team and possible re-merge node layouts.

In some cases, the content management techniques set forth above may be at least partially implemented using various templates, such as node templates and task templates. In some cases, node templates and task templates may be merged into different types of a single general object. Also, in some cases, the employed templates may include both general and specific templates. As an example, in some cases, a game designer may create one or more general node templates for use in association with a content item. In some cases, this may be done only once, such as at the initiation or earlier stages of a playing of a content item. In other cases, this may be done multiple times. For example, one or more general node templates may be added to a content item while the content item is being played. In some cases, a general node template may become available when it becomes connected to other nodes and its associated prerequisites for availability, such as those described above, are satisfied.

In some cases, a general node template may reference one or more specific nodes that may be selected for use with an associated content item or content item portion. Also, in some cases, a general node template may represent a node sub-layout that may, for example, include one or more other node templates, which themselves may also reference other node templates. A general node template may, for example, represent a specific or general task template, a list of tasks from which one or more tasks may be chosen, one or more sub-nodes or a sub-layout of other general or specific nodes or a list from which any of these features may be selected. In some cases, a general node template may be available or unavailable to all participants or to one or more specific participants. Also, in some cases, a general node template may include parameters and/or task characteristics for associated tasks such as participants to whom the tasks can be assigned, an indication of other tasks upon whose completion an availability of associated tasks are based, and other prerequisites for availability of associated tasks.

As another example, a general task template may, in some cases, be a type of node that may itself include a list of one or more general task templates to select from. One or more of the listed general task templates may be selected for assignment to one or more participants. A general task template may also, for example, include an associated specific task template. A general task template may also, for example, include a set of task templates that must all be completed in sequence, in parallel by multiple participants or in any other defined or undefined order.

In addition to general task templates, specific task templates may also be employed. A specific task template may include, for example, a list or other identification of a set of one or more associated parameters, such as those described above. In some cases, one or more of the associated parameters may each have a corresponding type, a specific value, a list of specific values from which a corresponding specific value may be selected or a range of values. As set forth above, some examples of associated parameters may include a number of participants required to complete one or more actions or action paths, gameplay type, type of location or terrain (e.g., mountain, forest, town, water), specific region within an associated virtual geography (e.g., specific country or town), a preferred participant skill or experience level, assigned participants or groups of participants and a date and/or time range within which the task is available. A gameplay type may indicate, for example, game specific types of play or goals (e.g., capture the flag, race, action, stealth, melee attack, raid, etc.). As also set forth above, in some cases, one or more specific values and/or value ranges may be selected and/or adjusted based on content item characteristics such as those described in detail above.

Thus, one or more tasks may each have one or more associated task templates that may be used, for example, for setting various parameters associated with each task. A task template may, for example, be used to assign a particular task to a particular participant, and the particular task may be performed in accordance with associated parameters such a specific location or area within a virtual geography, specific actions or action paths for completion, a specific gameplay type and other associated parameters.

Figure 10:
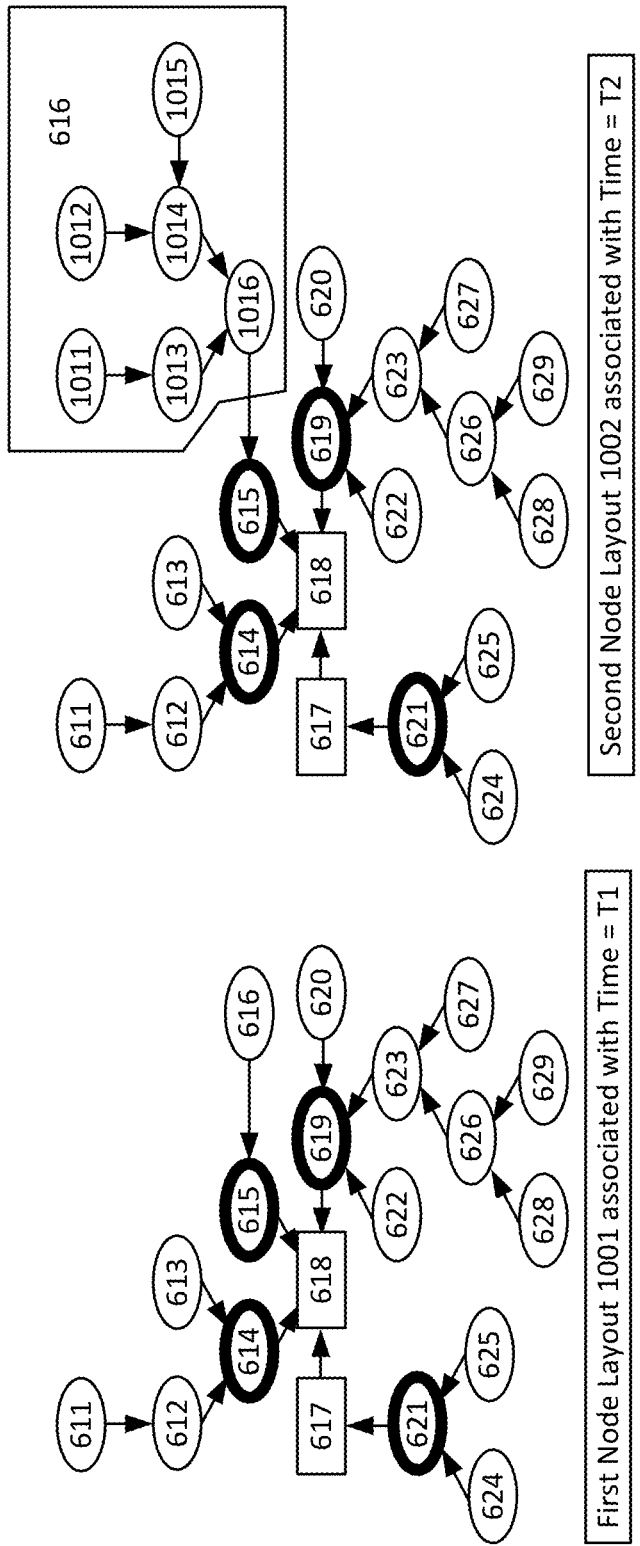
FIG. 10 is a diagram illustrating an example expansion of a node in a node layout.

In some cases, node templates and/or task templates may be used to add nodes to a node layout by expanding an existing node within a node layout. FIG. 10 is a diagram illustrating an example expansion of a node in a node layout. As shown, FIG. 10 includes a first node layout 1001 and a second node layout 1002. By comparing first node layout 1001 with second node layout 1002, it can be seen that node 616 has expanded from a single node in first node layout 1001 to a six node sub-layout in second node layout 1002. The six node sub-layout in second node layout 1002 includes nodes 1011-1016. In some examples, nodes 1011-1016 may be selected from a list of available nodes within a template corresponding to node 616.

FIG. 10 indicates that first node layout 1001 is associated with Time T1, while second node layout 1002 is associated with Time T2. In an example scenario, Time T1 may occur in the earlier stages of a playing of a content item, while Time T2 may occur in the later stages of a playing of a content item. In some cases, at Time T1, node 616 may include or otherwise be associated with a list of available nodes from which one or more nodes may be selected for inclusion in an associated content item portion. As the playing of the content item portion progresses from Time T1 to Time T2, nodes 1011-1016 may be selected from the list of available nodes associated with node 616. In some cases, nodes 1011-1016 may be selected from the list based on content item characteristics such as those described above. For example, nodes 1011-1016 may have associated tasks with task characteristics that match participant characteristics for one or more participants to which node 616 is assigned.

Figure 11:
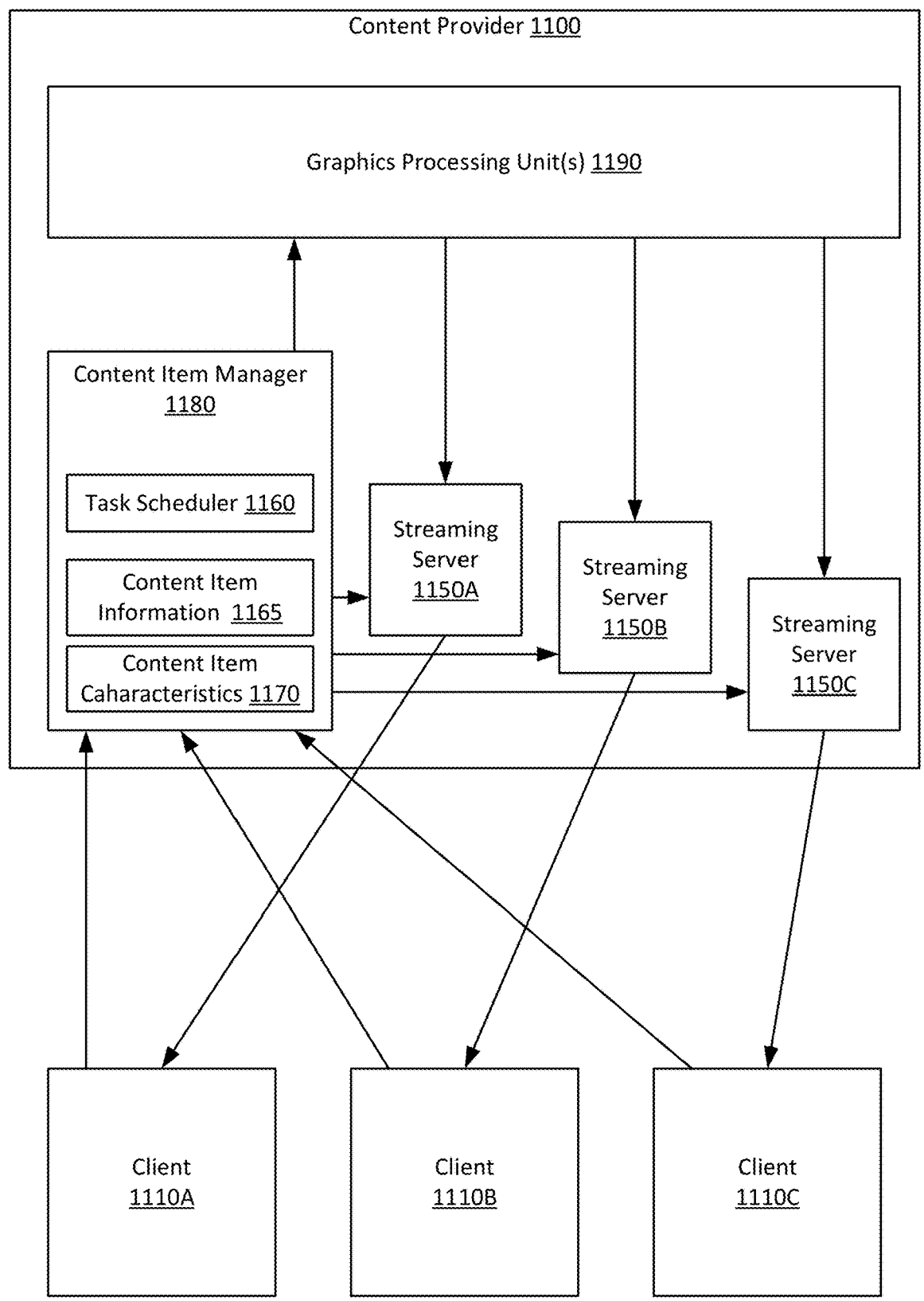
FIG. 11 is a diagram illustrating an example content management system.

Thus, various example techniques are set forth above for management of content. An example content management system in accordance with the disclosed techniques is depicted in FIG. 11. As shown, FIG. 11 includes clients 1110A-C in communication with content provider 1100. As should be appreciated, while three clients 1110A-C are shown in FIG. 11, any number of different clients may be used in accordance with the disclosed techniques. Clients 1110A-C may, for example, each participate in a transmission session of a particular content item. Clients 1110A-C each receive a transmission of a respective presentation of the content item from a respective one of three streaming servers 1150A-C. It is noted, however, that the disclosed techniques are not limited to the use of streaming technology or to the use of separate servers for transmission to each client. Rather, any number of servers may be employed in accordance with the present techniques for transmission to any number of different clients. The content item presentations transmitted to clients 1110A-C is rendered by one or more graphics processing units 1190. As should be appreciated, graphics processing units 1110A-C are merely one example type of processing component that may be used to process and provide content for presentation to participants. In addition or as an alternative to graphics processing units 1110A-C, any number of other processing components may also be employed to process and provide content for presentation to participants. These other processing components may include, for example, audio processing components, other graphics and video processing components, video and audio encoders and decoders and many others. In some cases, content items may be rendered by one or more graphics processing units and/or other processing components at one or more of clients 1110A-C. In these cases, content provider 1100 may send instructions to the clients 1110A-C for rendering of the content items at the clients 1110A-C.

Content provider 1100 includes a content item manager 1180, which may perform various operations in association with the content management techniques disclosed herein. Content item manager 1180 may be, for example, a video game manager, which is a content item manager that manages video games. Content item manager 1180 may have access to various information including, for example, content item characteristics 1170 and content item information 1165. Content item characteristics 1170 are described in detail above. Content item information 1165 may include, for example, data associated with node layouts and associated tasks, actions and parameters, node and/or task templates and other associated data. Content item characteristics 1170 and content item information 1165 may be, for example, generated, collected, maintained and/or adjusted by content item manager 1180. As should be appreciated, various portions of content item characteristics 1170 and content item information 1165 may include shared or duplicative data.

As an example, content item information 1165 may include code or other stored information about available nodes, tasks, actions and/or parameters that may be selected for inclusion in a content item or content item portion. Content item information 1165 may also include indications of the nodes, tasks, actions and/or parameters that are currently selected for inclusion in a content item or content item portion. As set forth above, in some cases, nodes, tasks, actions and/or parameters may be selected for inclusion in a content item prior to playing of the content item, at the initiation of playing of the content item and/or during the playing of a content item. In some cases, the selected nodes, tasks, actions and/or parameters may also be adjusted prior to playing of the content item, at the initiation of playing of the content item and/or during the playing of a content item. As also set forth above, in some cases, various nodes, tasks, actions and/or parameters may be selected for inclusion in a content item or content item portion and/or adjusted based on content item characteristics 1170.

Some operations performed by content item manager 1180 may include, for example, collection of content item characteristics, generation of one or more story arcs including selection of included tasks and associated actions and parameters, generation of one or more node layouts and associated data, monitoring progress of one or more participants and teams, adjustment of various tasks and associated actions and parameters, adjustment of one or more node layouts and associated data, generating instructions for providing portions of a content item for presentation to one or more participants and the like. Additionally, as shown, in FIG. 11 content item manager 1180 includes a task scheduler 1160, which, as set forth above, may perform operations such as assigning participants to various available tasks. As also set forth above, the assignment of participants to tasks may, in some cases, be performed based on various content item characteristics 1170 including, for example, comparisons of various participant characteristics to various task characteristics.

Figure 12:
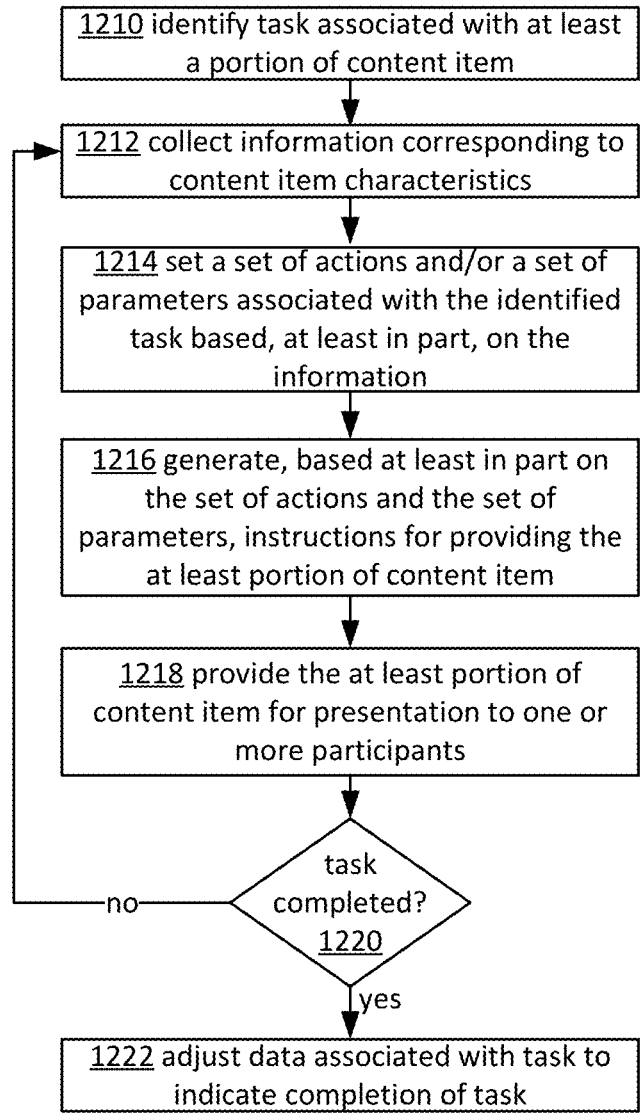
FIG. 12 is a flowchart depicting an example procedure for task management in accordance with the present disclosure.

FIG. 12 is a flowchart depicting an example procedure for task management in accordance with the present disclosure. In some cases, operations 1210, 1212, 1214, 1216, 1220 and 1222 may be, for example, performed by content item manager 1180 of FIG. 11, while operation 1218 may be, for example, performed by graphics processing unit(s) 1190 of FIG. 11 and/or other processing components. At operation 1210, a task associated with at least a portion of a content item is identified. A task may be associated with a content item or content item portion by, for example, being included within the content item or content item portion. As set forth above, various tasks may be included within various portions of a content item such as particular story arcs. As also set forth above, various tasks may be assigned to various participants or groups of participants such as teams or factions. In some cases, a task may be identified by a task scheduler that assigns various participants to available tasks. Also, in some cases, a task may be identified based on its inclusion in a data collection associated with a content item or content item portion such as an associated node layout.

At operation 1212, information corresponding to content item characteristics is collected. Content item characteristics, including, for example, participant characteristics, task characteristics and other characteristics, are described in detail throughout the disclosure above, and these descriptions are not repeated here. As set forth above, content item characteristics may be collected based on, for example, information transmitted from content item participants operating one or more connected client computing devices. This may include, for example, state information associated with the content item as well as personal information associated with the participants themselves. Also, in some cases, participant characteristics may be determined and/or adjusted by software or algorithms based on an observed or collected history of participant behavior with respect to one or more content items. Additionally, content item characteristics may also be collected, for example, from other sources such as files or code included within the content item itself, information from one or more content item developers or information from third parties or other associated entities.

At operation 1214, a set of one or more actions and/or a set of one or more parameters associated with the identified task is set based, at least in part, on the content item characteristics information collected at operation 1212. Operation 1214 may include, for example, adding, changing and/or removing one or more actions in the set of one or more actions and/or one or more parameters in the set of one or more parameters. In some cases, all or various portions of operation 1214 may be performed using one or more task templates and/or node templates such as described above. Operation 1214 may, for example, include an initial setting (i.e., generating) of the set of one or more actions and/or the set of one or more parameters. The initial setting (i.e., generating) of the set of one or more actions and/or the set of one or more parameters may include selecting and adding one or more actions to the set of one or more actions and/or one or more parameters to the set of one or more parameters. Operation 1214 may also, for example, include a modified setting (i.e., adjusting) of the set of one or more actions and/or the set of one or more parameters. The modified setting (i.e., adjusting) of the set of one or more actions and/or the set of one or more parameters may include adding, changing and/or removing one or more actions in the set of one or more actions and/or one or more parameters in the set of one or more parameters.

As set forth above, in some cases, an action may be added to the set of actions associated with a task when the action has action characteristics that match participant characteristics for participants to which a task is assigned. For example, actions may be selected that may match interests, preferences, skill levels, play style, demographics and other characteristics of a participant or group of participants to which a task is assigned. Also, in some cases, if the participant characteristics change, then the actions may be changed to match the change in participant characteristics. Additionally, in some cases, actions may be removed and new actions may be selected to match the change in participant characteristics. As also set forth above, in some cases, parameters may be added to the set of parameters associated with a task based on a goal of having desired quantities and/or percentages of participants perform desired actions and tasks within desired time periods. Also, in some cases, if a task's associated participant characteristics change, then the parameters may be adjusted to match the change in participant characteristics. Additionally, in some cases, parameters may be removed and new parameters may be selected to match the change in participant characteristics. Some specific examples of adding, changing and/or removing actions and/or parameters based on content item characteristics are set forth above respect to FIGS. 3A, 3B, 4A, 4B, 5A and 5B.

It is noted that there is no requirement that operation 1214 must be performed every time that information corresponding to content item characteristics is collected. For example, in some cases, a collection of content item characteristics may include few, if any, relevant changes with respect to previously collected content item characteristics. In these and other cases, there may be no actions and/or parameters added, changed or removed in the associated sets of actions and parameters, and operation 1214 may be skipped.

At operation 1216, instructions are generated for providing the at least portion of the content item based, at least in part, on the set of actions and the set of parameters. For example, at operation 1216, instructions may be generated that enable the task identified at operation 1210 to be at least partially performed by one or more participants in accordance with the set of actions and the set of parameters. In particular, instructions may be generated for creating one or more scenes that correspond to the identified task based, at least in part, on the associated actions and parameters. In some cases, various attributes of the scenes may also be determined based, at least in part, on the associated actions and parameters. For example, in some cases, the contents, sequence, timing and duration of the scenes may be determined based, at least in part, on the associated actions and parameters. In particular, various characters, activities, weapons, resources, geographic locations, settings, play styles, level of resistance and other information associated with the scenes may be determined based, at least in part, on the associated actions and parameters. Furthermore, for example, the activities and interactions of various characters and other objects within a scene may be determined based, at least in part, on the associated actions and parameters. For example, in a scene corresponding to an attack task, one or more sniper characters may be included in the scene and positioned with rifles around a perimeter of the scene, while one or more combat troop characters may be included in the scene and may engage in combat with one another in a central area of the scene. The positions and interactions of the sniper characters and combat troop characters may be determined based, at least in part, on the associated actions and parameters. Additionally, the participants and/or groups of participants to which the various scenes are presented may be determined based, at least in part, on the associated actions and parameters. For example, in some cases, images of a scene may be presented to one or more participants that control characters that are included within a scene based, at least in part, on the associated actions and parameters. As another example, in some cases, when a quantity of participants required to complete an action path is reduced, the task may become immediately completed, and participants that were still in the process of attempting to complete an action path associated with the task may be re-assigned to other tasks. This may cause, for example, scenes associated with the completed task to cease to be presented to the re-assigned participants. The re-assigned participants may subsequently be presented with scenes associated with the other tasks to which they are re-assigned.

At operation 1218, the at least portion of the content item is provided for presentation to one or more participants. Operation 1218 may be performed based, at least in part, on the instructions generated at operation 1216. For example, at operation 1218, one or more graphics processing units and/or other processing components may render or otherwise provide one or more images in accordance with one or more scenes generated in association with operation 1216. In some cases, the rendered images may be transmitted from a content provider to one or more participants operating connected client devices. In some other cases, the images may be rendered by one or more graphics processing units and/or other processing components at one or more connected client devices based on information transmitted from a content provider. The rendered images may then be presented to the one or more participants via the connected client devices. At operation 1220, it is determined whether the task identified at operation 1210 is completed. As set forth above, a completion of a task may be determined based, at least in part, on the associated set of one or more actions and the associated set of one or more parameters that are set at operation 1214. Some detailed examples of how a completion of a task may be determined are described above and are not repeated here. If, the task is not completed, then the process loops back to operation 1212. If the task is completed, then, at operation 1222, data associated with the task is adjusted to indicate a completion of the task. For example, as set forth above, a node layout may include a node associated with the task, and data within or otherwise associated with the node may be adjusted to indicate that the task is completed.

Figure 13:
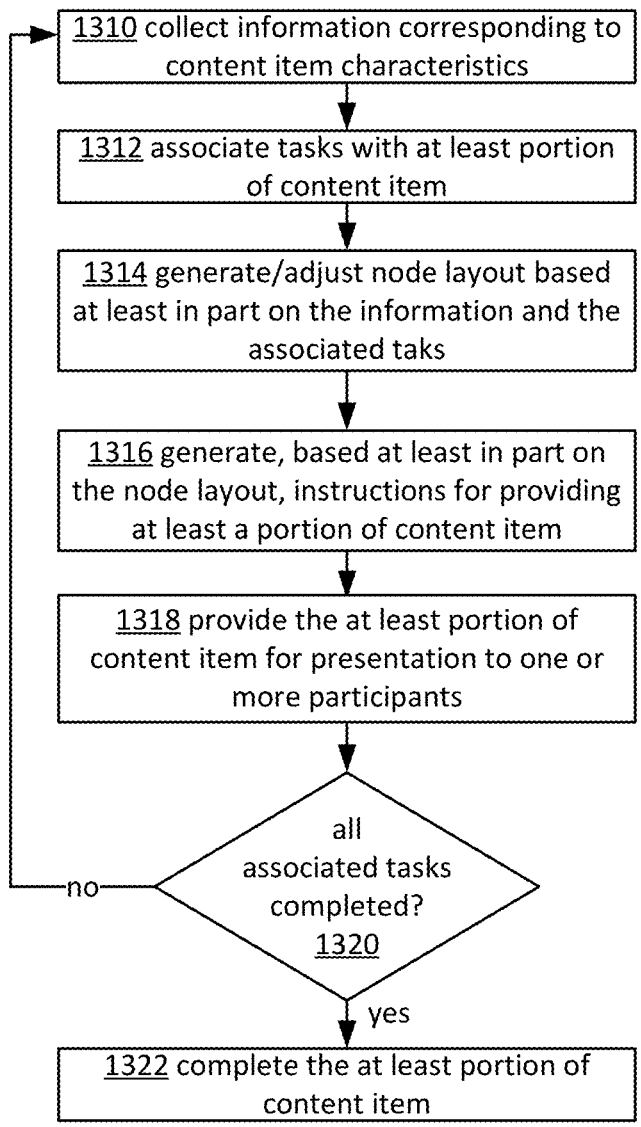
FIG. 13 is a flowchart depicting an example procedure for node layout management in accordance with the present disclosure.

FIG. 13 is a flowchart depicting an example procedure for node layout management in accordance with the present disclosure. In some cases, operations 1310, 1312, 1314, 1316, 1320 and 1322 may be, for example, performed by content item manager 1180 of FIG. 11, while operation 1318 may be, for example, performed by graphics processing unit(s) 1190 of FIG. 11 and/or other processing components. At operation 1310, information corresponding to content item characteristics is collected. The collection of content item characteristics is described in detail above and is not repeated here. At operation 1312, tasks are associated with at least a portion of a content item. Tasks may, for example, be associated with at least a portion of a content item based upon being selected for inclusion within the at least portion of the content item. As set forth above, in some cases, tasks may be selected and added to a content item or content item portion based, at least in part, on content item characteristics such as those collected at operation 1310. In some cases, tasks may be selected and added to a content item or content item portion by matching task characteristics to participant characteristics for participants associated with the content item or content item portion. For example, tasks may be added that may match interests, preferences, skill levels, play style, demographics and other characteristics of a participant or group of participants.

At operation 1314, a node layout is generated or adjusted based at least in part on the information collected at operation 1310 and the tasks associated with the at least portion of the content item at operation 1312. In some cases, the node layout may be generated during the first iteration of operation 1314, while the node layout may be adjusted during subsequent iterations of operation 1314. In some cases, all or various portions of operation 1314 may be performed using one or more task templates and/or node templates such as described above. As set forth above, each node within a node layout may, for example, have at least one associated task within a respective content item or content item portion. The node layout may, for example, at least partially indicate one or more relationships between two or more nodes within the node layout. A relationship between nodes may be based on, for example, virtual geography corresponding to tasks associated with the nodes. A relationship between nodes may also be based on, for example, an availability of a task associated with one node being based, at least in part, on a completion of one or more other tasks associated with one or more other nodes. In some cases, the node layout may include an indication of whether a task associated with each node is available to at least one participant or is not available to any participants. Also, in some cases, the node layout may include an indication of whether a task associated with each node has been completed or is not yet completed. In addition to the node layout itself, associated data corresponding to one or more nodes of the node layout may also, in some cases, be generated and adjusted based at least in part on the information collected at operation 1310 and the tasks associated with the at least portion of the content item at operation 1312.

As set forth above, in some cases, the task characteristics for a task may indicate one or more other tasks whose availability is at least partially based upon a completion of the task. Also, in some cases, the task characteristics for a task may indicate one or more other tasks upon whose completion the availability of the task is at least partially based. This task information and other collected content item characteristics information may be used, for example, to generate and adjust the node layout. Furthermore, for example, task characteristics may sometimes indicate a virtual geography associated with one or more tasks that may also be used to generate and adjust the node layout. Additionally, a sequence in which one or more tasks are made available to a particular participant or group of participants may also, in some cases, be determined based upon participant characteristics such as interests, preferences, skill levels, play style, demographics and other characteristics.

At operation 1316, instructions are generated for providing the at least portion of the content item based, at least in part, on the set of actions and the set of parameters. For example, at operation 1316, instructions may be generated that enable one or more available tasks associated with nodes in the node layout to be at least partially performed by one or more participants. In particular, instructions may be generated for creating scenes that correspond to the one or more available tasks. Some examples techniques for creating one or more scenes that correspond to a task are described above, for example, with reference to operation 1216 of FIG. 12. The node layout may, for example, be used to determine which scenes associated with which available tasks should be presented to which of one or more participants associated with the at least portion of the content item. For example, as set forth above, the node layout may be used to assign one or more participants to one or more available tasks by, for example, comparing and matching various participant characteristics to various task characteristics. In some cases, each participant that is currently assigned to a particular task may be presented with an image that is rendered based on a created scene that corresponds to the particular task.

At operation 1318, the at least portion of the content item is provided for presentation to one or more participants. Operation 1318 may be performed based, at least in part, on the instructions generated at operation 1316. For example, at operation 1318, one or more graphics processing units and/or other processing components may render or otherwise provide one or more images in accordance with one or more scenes generated in association with operation 1316. In some cases, the rendered images may be transmitted from a content provider to one or more participants operating connected client devices. In some other cases, the images may be rendered by one or more graphics processing units and/or other processing components at one or more connected client devices based on information transmitted from a content provider. The rendered images may then be presented to the one or more participants via the connected client devices. At operation 1320, it is determined whether all of the tasks associated with the at least portion of the content item at operation 1312 are completed. As set forth above, a completion of each task may be determined based, at least in part, on an associated set of one or more actions and the associated set of one or more parameters. If all of the associated tasks are completed, then, at operation 1322, the at least portion of the content item is completed. As set forth above, in some cases, a content item or a portion of a content item may be designed such that it continues indefinitely and/or to run at least temporarily without a defined end point. In such cases, operation 1322 may not be included as part of the process depicted in FIG. 13.

If the associated tasks are not completed, then the process loops back to operation 1310. As should be appreciated, upon looping back to operation 1310, the process may repeat itself. In particular, upon being repeated, updated information corresponding to content item characteristics may be collected at operation 1310. As set forth above, the updated content item characteristic information collected at repeated operation 1310 may be used to determine whether tasks should be added, changed or removed within the at least portion of the content item. Accordingly, when operation 1312 is repeated, newly added and/or changed tasks may, for example, be associated and/or re-associated with the at least portion of the content item. Additionally, for example, removed tasks may be removed from association with the at least portion of the content item.

The updated content item characteristic information collected at repeated operation 1310 may be also used to adjust a node layout as set forth in detail above. Accordingly, upon being repeated, operation 1314 may include adjusting of the node layout and, potentially, associated data based at least in part on the information collected at repeated operation 1310 and the tasks associated with the at least portion of the content item at repeated operation 1312. As set forth above, a node layout may be adjusted by, for example, adding, changing or deleting nodes or by changing a relationship between one or more nodes. In some cases, nodes may be added to a node layout by expanding a single existing node to include multiple different nodes such as described above with reference to FIG. 10.

Additionally, in some cases, upon repeating the process of FIG. 13, operation 1312 and/or operation 1314 may be skipped. For example, in some cases, when operation 1310 is repeated, a collection of content item characteristics may include few, if any, relevant changes with respect to previously collected content item characteristics. In these and other cases, there may be no changes to the associated tasks and/or the relationships between the associated tasks with respect to the at least portion of the content item.

Each of the processes, methods and algorithms described in the preceding sections may be embodied in, and fully or partially automated by, code modules executed by one or more computers or computer processors. The code modules may be stored on any type of non-transitory computer-readable medium or computer storage device, such as hard drives, solid state memory, optical disc and/or the like. The processes and algorithms may be implemented partially or wholly in application-specific circuitry. The results of the disclosed processes and process steps may be stored, persistently or otherwise, in any type of non-transitory computer storage such as, e.g., volatile or non-volatile storage.

The various features and processes described above may be used independently of one another, or may be combined in various ways. All possible combinations and subcombinations are intended to fall within the scope of this disclosure. In addition, certain methods or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel or in some other manner. Blocks or states may be added to or removed from the disclosed example embodiments. The example systems and components described herein may be configured differently than described. For example, elements may be added to, removed from or rearranged compared to the disclosed example embodiments.

It will also be appreciated that various items are illustrated as being stored in memory or on storage while being used, and that these items or portions thereof may be transferred between memory and other storage devices for purposes of memory management and data integrity. Alternatively, in other embodiments some or all of the software modules and/or systems may execute in memory on another device and communicate with the illustrated computing systems via inter-computer communication. Furthermore, in some embodiments, some or all of the systems and/or modules may be implemented or provided in other ways, such as at least partially in firmware and/or hardware, including, but not limited to, one or more application-specific integrated circuits (ASICs), standard integrated circuits, controllers (e.g., by executing appropriate instructions, and including microcontrollers and/or embedded controllers), field-programmable gate arrays (FPGAs), complex programmable logic devices (CPLDs), etc. Some or all of the modules, systems and data structures may also be stored (e.g., as software instructions or structured data) on a computer-readable medium, such as a hard disk, a memory, a network or a portable media article to be read by an appropriate drive or via an appropriate connection. The systems, modules and data structures may also be transmitted as generated data signals (e.g., as part of a carrier wave or other analog or digital propagated signal) on a variety of computer-readable transmission media, including wireless-based and wired/cable-based media, and may take a variety of forms (e.g., as part of a single or multiplexed analog signal, or as multiple discrete digital packets or frames). Such computer program products may also take other forms in other embodiments. Accordingly, the present invention may be practiced with other computer system configurations.

Conditional language used herein, such as, among others, "can," "could," "might," "may," "e.g." and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having" and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some or all of the elements in the list.

While certain example embodiments have been described, these embodiments have been presented by way of example only and are not intended to limit the scope of the inventions disclosed herein. Thus, nothing in the foregoing description is intended to imply that any particular feature, characteristic, step, module or block is necessary or indispensable. Indeed, the novel methods and systems described herein may be embodied in a variety of other forms; furthermore, various omissions, substitutions and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

What is claimed is:

1. A system comprising:
   one or more processors; and
   one or more memories to store a set of instructions, which if executed by the one or more processors, causes the one or more processors to perform operations comprising:
   generating a node layout, wherein the node layout comprises a plurality of nodes associated with a plurality of tasks in a video game, wherein the node layout indicates availability of one or more of the plurality of tasks to one or more participants of the video game based at least in part on a completion of one or more other tasks of the plurality of tasks;
   collecting information corresponding to a performance of the one or more participants of the video game;
   adjusting the node layout during playing of the video game, the adjusting comprising adding or removing a first node to or from the node layout based on the performance of the one or more participants; and
   providing, based at least in part on the node layout, at least a portion of the video game for presentation to the one or more participants of the video game.

2. The system of claim 1, wherein the node layout comprises indications of whether each of the plurality of tasks is available or unavailable.

3. The system of claim 2, wherein the operations further comprise:
   detecting that a participant has joined a playing of the video game; and
   responsively assigning the participant to a task that is indicated by the node layout as being available, wherein the participant is assigned to the task based, at least in part, on a comparison of one or more characteristics associated with the participant to one or more characteristics associated with the task.

4. The system of claim 1, wherein each of the plurality of tasks has one or more associated task templates that are used for setting at least one parameter associated with each of the plurality of tasks.

5. The system of claim 1, wherein an availability of at least one task is based, at least in part, on a virtual geography corresponding to the at least one task.

6. The system of claim 1, wherein the node layout comprises indications of whether each of the plurality of tasks is completed or uncompleted.

7. The system of claim 1, wherein the information further corresponds to at least one of participant quantity, participant skill level, participant preferences, participant interests, participant demographics, or participant play style.

8. The system of claim 5, wherein the node layout at least partially indicates one or more relationships between two or more nodes of the plurality of nodes.

9. The system of claim 8, wherein the one or more relationships comprise an availability of a task associated with a node being based, at least in part, on a completion of at least one other task associated with at least one other node.

10. A method comprising:
    generating, by one or more computing devices, a node layout, wherein the node layout comprises a plurality of nodes associated with a plurality of tasks in a video game, wherein the node layout indicates availability of one or more of the plurality of tasks to one or more participants of the video game based at least in part on a completion of one or more other tasks of the plurality of tasks;
    collecting, by the one or more computing devices, information corresponding to a performance of the one or more participants of the video game;
    adjusting, by the one or more computing devices, the node layout during playing of the video game, the adjusting comprising adding or removing a first node to or from the node layout based on the performance of the one or more participants;
    providing, by the one or more computing devices, based at least in part on the node layout, at least a portion of the video game for presentation to the one or more participants of the video game.

11. The method of claim 10, wherein the node layout comprises indications of whether each of the plurality of tasks is available or unavailable.

12. The method of claim 11, further comprising:
   detecting that a participant has joined a playing of the video game; and
   responsively assigning the participant to a task that is indicated by the node layout as being available, wherein the participant is assigned to the task based, at least in part, on a comparison of one or more characteristics associated with the participant to one or more characteristics associated with the task.

13. The method of claim 10, wherein each of the plurality of tasks has one or more associated task templates that are used for setting at least one parameter associated with each of the plurality of tasks.

14. The method of claim 10, wherein an availability of at least one task is based, at least in part, on a virtual geography corresponding to the at least one task.

15. The method of claim 10, wherein the node layout comprises indications of whether each of the plurality of tasks is completed or uncompleted.

16. The method of claim 10, wherein the information further corresponds to at least one of participant quantity, participant skill level, participant preferences, participant interests, participant demographics, or participant play style.

17. The method of claim 16, wherein the node layout at least partially indicates one or more relationships between two or more nodes of the plurality of nodes.

18. The method of claim 17, wherein the one or more relationships comprise an availability of a task associated with a node being based, at least in part, on a completion of at least one other task associated with at least one other node.

19. One or more non-transitory computer-readable storage media having stored thereon instructions that, upon execution on at least one compute node, cause the at least one compute node to perform operations comprising:
   generating a node layout, wherein the node layout comprises a plurality of nodes associated with a plurality of tasks in a video game, wherein the node layout indicates availability of one or more of the plurality of tasks to one or more participants of the video game based at least in part on a completion of one or more other tasks of the plurality of tasks;
   collecting information corresponding to a performance of the one or more participants of the video game;
   adjusting the node layout during playing of the video game, the adjusting comprising adding or removing a first node to or from the node layout based on the performance of the one or more participants;
   providing, based at least in part on the node layout, at least a portion of the video game for presentation to the one or more participants of the video game.

20. The one or more non-transitory computer-readable storage media of claim 19, wherein the node layout comprises indications of whether each of the plurality of tasks is available or unavailable;
   the performance of the one or more participants; and
   providing, based at least in part on the node layout, at least a portion of the video game for presentation to the one or more participants of the video game.

* * * * *